(12) United States Patent
Gibbs et al.

(10) Patent No.: US 7,301,633 B2
(45) Date of Patent: Nov. 27, 2007

(54) HIGH-THROUGHPUT CHIRAL DETECTOR AND METHODS FOR USING SAME

(75) Inventors: Phillip Ray Gibbs, Atlanta, GA (US); Rick P. Trebino, Atlanta, GA (US); Andreas Sebastian Bommarius, Atlanta, GA (US); Mark W. Kimmel, Lawrenceville, GA (US)

(73) Assignee: Georgia Institute of Technology, Atlanta, GA (US)

( * ) Notice: Subject to any disclaimer, the term of this patent is extended or adjusted under 35 U.S.C. 154(b) by 221 days.

(21) Appl. No.: 10/491,094

(22) PCT Filed: Oct. 1, 2002

(86) PCT No.: PCT/US02/31279

§ 371 (c)(1),
(2), (4) Date: Dec. 20, 2004

(87) PCT Pub. No.: WO03/029790

PCT Pub. Date: Apr. 10, 2003

(65) Prior Publication Data

US 2005/0094144 A1 May 5, 2005

Related U.S. Application Data

(60) Provisional application No. 60/382,413, filed on May 21, 2002, provisional application No. 60/326,329, filed on Oct. 1, 2001.

(51) Int. Cl.
*G01J 4/00* (2006.01)
(52) U.S. Cl. ...................................... 356/369; 356/367
(58) Field of Classification Search ................ 356/367, 356/369
See application file for complete search history.

(56) References Cited

U.S. PATENT DOCUMENTS

| | | | | |
|---|---|---|---|---|
| 6,046,805 | A * | 4/2000 | Kawamura et al. | 356/244 |
| 6,166,807 | A * | 12/2000 | Kawamura et al. | 356/364 |
| 6,466,320 | B1 * | 10/2002 | Kawamura et al. | 356/364 |
| 6,620,622 | B1 * | 9/2003 | Kawamura | 436/164 |
| 6,750,063 | B1 * | 6/2004 | Kawamura | 436/164 |

* cited by examiner

*Primary Examiner*—Roy M. Punnoose
(74) *Attorney, Agent, or Firm*—Robert W Strozier

(57) ABSTRACT

A new generation polarimetry apparatus and methodology is disclosed, which involve passing polarized light through a sample including a chiral analyte, where the analyte is under the influence of a periodically varying magnetic field. The apparatus also utilizes optical heterodyne detection and lock-in detection at higher order harmonics of the magnetic field modulation frequency to improve sensitivity and detection limits of optical properties of chiral analytes.

19 Claims, 8 Drawing Sheets

FIG. 7A
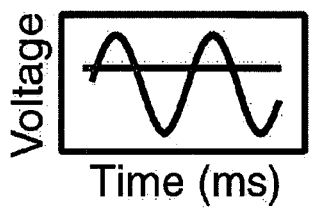
Optical activity ≠ 0.
Verdet const = 0.
$A_f = 0$.
FIG. 7B
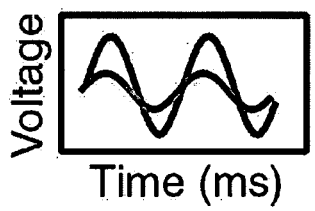
Optical activity = 0.
Verdet const ≠ 0.
$A_f \neq 0; \phi_f = 0$.
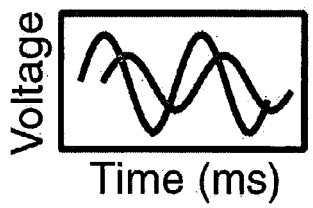
Optical activity ≠ 0.
Verdet const ≠ 0.
$A_f \neq 0; \phi_f \neq 0$.
FIG. 7C
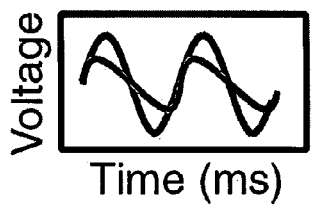
**Higher-order
Verdet const ≠ 0.**
$A_f \neq 0; A_{2f} \neq 0$.
FIG. 7D

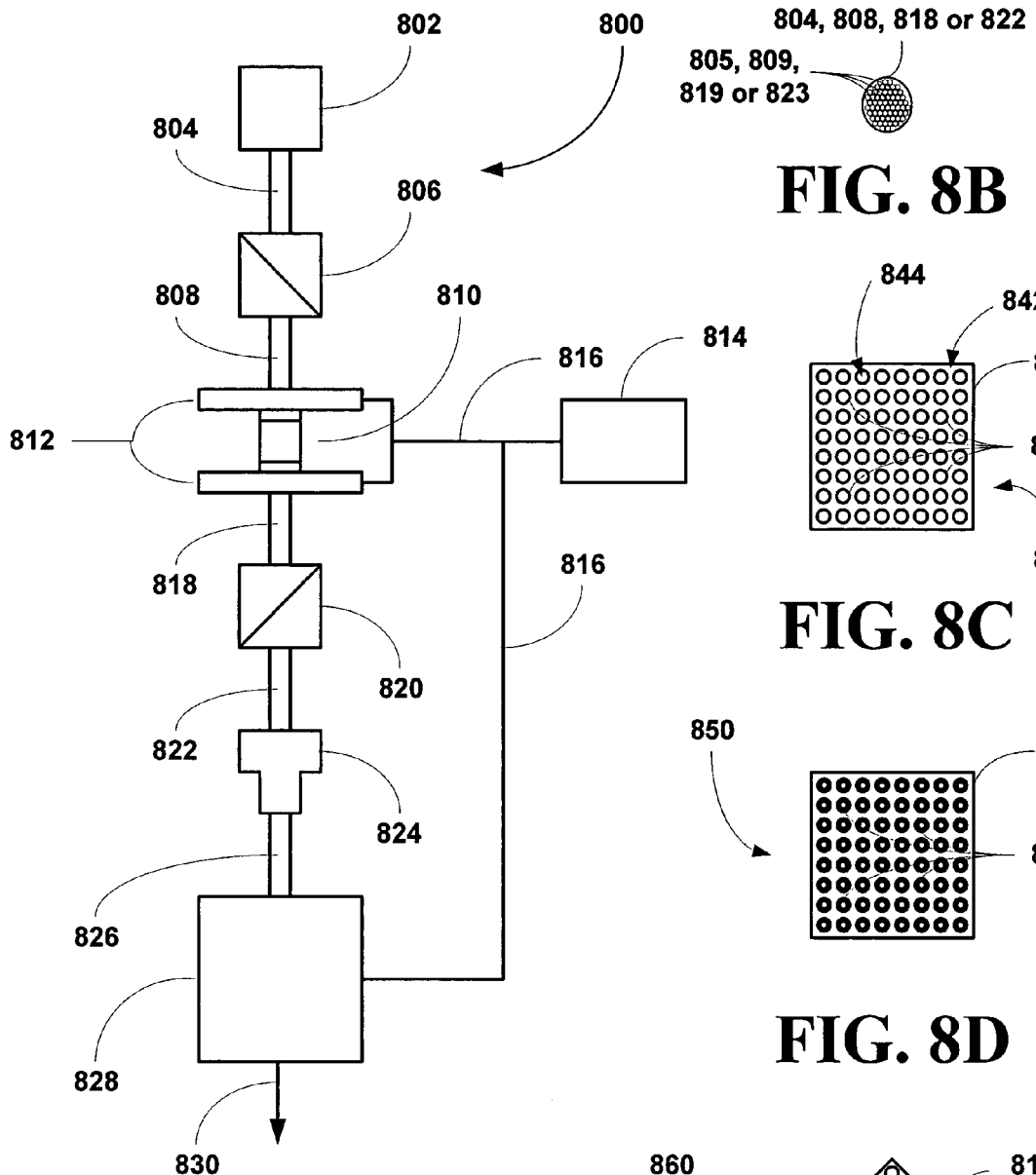
FIG. 8A
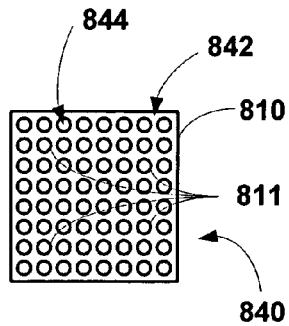
FIG. 8B
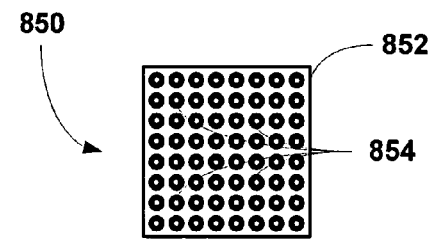
FIG. 8C
FIG. 8D
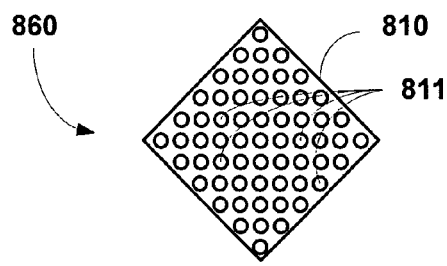
FIG. 8E

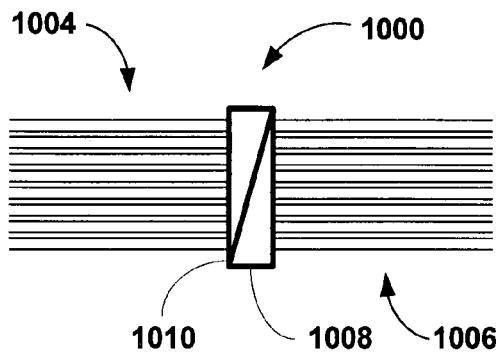
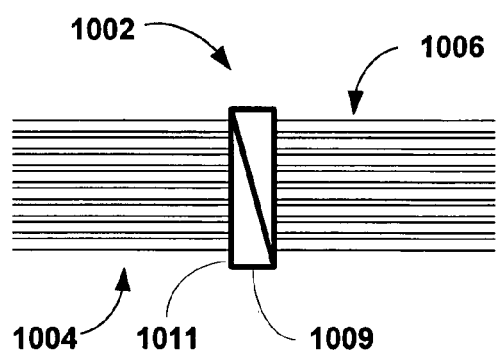
FIG. 10A  FIG. 10B
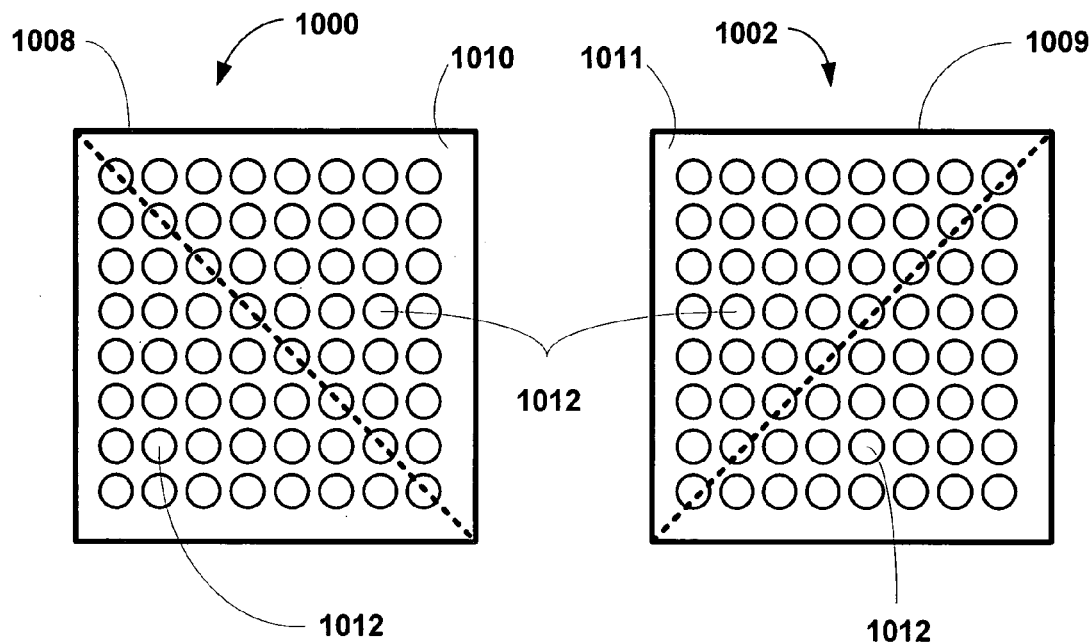
FIG. 10C  FIG. 10D

HIGH-THROUGHPUT CHIRAL DETECTOR AND METHODS FOR USING SAME

RELATED APPLICATIONS

This application claims provisional priority to the following U.S. Provisional Patent Application Ser. Nos.: 60/326,329, filed Oct. 1, 2001, and 60/382,413, filed May 21, 2002.

BACKGROUND OF THE INVENTION

1. Field of the Invention

The present invention relates to an apparatus for rapid screening of chiral molecules, to method for making the apparatus and to methods for using the apparatus to screen chiral molecules, especially, catalyst, bio-catalyst, bio-molecules such as polypeptides, proteins, enzymes, ribozymes, or the like or mixtures or combination thereof.

More particularly, the present invention relates to an apparatus including a sample cell, a polarized light source for supply polarized light to a sample in the cell, a magnetic field generator surrounding the cell for applying a time varying magnetic field to a sample in the cell, an analyzer for analyzing the transmitted light from the sample, a detector for detecting the output of the analyzer and generating a sample output signal, a lock-in amplifier for receiving the detector output signal and generating an amplitude and a phase of the detector output signal and a power supply for supplying a time varying electrical input to the magnetic field generator and for supplying a reference input or lock input to the lock-in amplifier. The present invention also relates to methods for making and using the apparatus.

2. Description of the Related Art

Many diseases are still without an effective treatment today, and others have evolved resistances requiring new therapeutic agents to be developed. Among these ailments are the neurodegenerative diseases, autoimmune diseases, cancer, viral diseases, fungal infections, tropical parasitic diseases, in addition to emerging antibiotic resistant pathogenic bacterial strains. Treatment of many such diseases will depend on inhibiting a key enzyme or enzymes. Examples include: cathepsin D as a novel treatment for Alzheimer's[7], matrix metalloproteases (MMPs) for rheumatoid arthritis[50] and early stage cancers[33,70], HIV integrase[13], HIV protease[48], HIV reverse transcriptase[49] in the cases of AIDS, cytochorome P450 enzyme lanosterol 14α-demethylase for fungal infections[12,65], glutathione reductase for the treatment of Malaria[40], cruzain and rodesian for the treatment of the trypanosomal diseases Chargas disease, African sleeping sickness, and Nagana[19], and new antibiotics for targeting bacterial cell wall synthesis, protein synthesis, and DNA replication[14].

Fortunately, the advent of combinatorial chemistry has helped augment the pharmaceutical industries' capacity to develop new lead compounds to treat these diseases. Coupled with the recent advances in bioinformatics for identifying new targets, there exists tremendous potential for developing effective small-molecule therapeutic agents, not only for these diseases, but also for those ailments for which no effective treatment exists[21].

In the effort to develop these discovery candidates for medical applications, an important observation is that the vast majority of useful drugs contain one or several chiral centers[55]. The wrong enantiomer can unfortunately cause harmful side effects, so very high enantiomeric purity of therapeutics is also essential[12]. The observation that chirality can play a major role in the toxicity and specificity of therapeutic agents was first made in 1956 by Carl Pfeiffer[45] and is commonly referred to as Pfeiffer's Rule which states ". . . the greater the difference between the pharmacological activity of the D and L isomers the greater is the specificity of the active isomer for the response of the tissue under test." Thus, both producing enantiomerically pure formulations and testing for enantiomeric purity are critical. Unfortunately, both of these activities remain significant challenges, even with the current state-of-the-art analytical instrumentation.

The realization that enantiomeric purity plays a critical role in the specificity and toxicity of pharmacological agents has prompted the Food & Drug Administration to increase its regulatory oversight into enantiomeric purity of approved pharmaceuticals. Recent FDA policy[71] requires that any drug component over 1% of total composition be tested with separate toxicology studies. Thus a racemic drug candidate would require separate trials for each enantiomer. While enantiomeric purity is not mandated by the FDA, the huge cost of clinical trials virtually ensures that pharmaceutical companies will develop enantiomerically pure drug candidates,[56] provided the enantiomers do not readily interconvert.

A variety of process solutions, such as resolution of racemates or asymmetric synthesis, are utilized by the pharmaceutical industry to provide these enantiomerically pure drugs. Owing to lack of suitable catalysts or insufficient selectivity, however, efficient enantioselective synthesis of these enantiomers remains a major challenge. As a result, resolution methods still dominate in industrial production[56]. This limits their transfer from therapeutic concept to cost-effective drugs on the market.

While recent progress in the area of biocatalysis to provide more stereoselective catalysts is encouraging[44], the number of enzymes commercially available remains limited. However, advances in the area of directed evolution and metabolic engineering show promise of changing this situation[68]. In some special cases, where screens have been established for specific substrate enantiomeric purity, directed evolution has proven to be capable of improving enantioselectivity of enzymes. Unfortunately these screens require expensive or modified reagents, and have only moderate (thousands/day) throughput[41]. Therefore not all compounds of interest are amenable to these approaches, and the low throughput limits the true utility of the directed evolution approach[4]. The same limitation applies to non-enzymatic combinatorial chemistry approaches, where large libraries must be screened for activity to determine successful chiral catalyst[22] or screening environmental samples for novel activity[64]. "You get what you screen for"[3] and to date no generally applicable method for high throughput enantiomeric purity screening is available to the researcher.

As, by definition, chiral molecules display optical rotation (they rotate the polarization of light, a property that is also called "optical activity"), polarimetry would seem to be an excellent technique for search and optimization of efficient enantioselective catalysts. However, polarimetry currently lacks several features essential for advantageous utilization in the development of chiral catalysts. Such features include sensitivity: the best polarizers are constructed from material (calcite) that cannot be grown in the laboratory. So naturally occurring calcite are commonly used, but it has imperfect optical quality and hence results in limited sensitivity. Also, polarimetry is one-dimensional, yielding only one parameter (the optical rotation) and hence is a weaker indicator than one would like: a multi-parameter result would be much more useful. Another needed feature is the ability to perform high-throughput screening: the best polarimeters utilize the highest quality calcite crystals, which allow only one sample to be measured at a time due to their small size (<20 mm×20 mm). In addition, current polarimeters require sample chambers with long path lengths (100 mm), relatively high sample concentrations (mg/mL), and long data-acquisition times, which allow only ten to twenty samples per hour. While larger dichroic sheet polarizers have been used to allow the screening of ~100 wells simultaneously by imaging[24,25,66], this technique lacks sensitivity due to the rather poor extinction coefficient (the ratio of light transmitted when the polarizers are crossed to that when they are parallel, an indicator of polarizer quality) of sheet polarizers.

Thus, there is a need in the art for a next-generation polarimeter apparatus and method that overcomes all these problems and which is suitable for rapid, accurate, and large-scale screening of catalysts or other chiral compounds including pharmaceuticals.

SUMMARY OF THE INVENTION

The present invention provides a next-generation polarimeter, CD and/or ORD apparatus and method using the new-generation polarimeter that overcomes all these problems and is suitable for rapid, accurate, and large-scale screening of chiral molecules such as chiral catalysts. The present invention applies several experimentally simple, but scientifically sophisticated, optical techniques developed for nonlinear-optical spectroscopy to polarimetry. These techniques include lock-in detection, the Faraday effect using a sinusoidally varying magnetic field, mid optical heterodyne detection (OHD). The present invention also involves use of the higher-order Faraday effects to aid in determining the a chirality of a substance.[60,61] In the present invention, the use of OHD and lock-in detection allows more sensitive detection of the second-order Faraday effect, and hence improved measurement of a substance's chirality. The improved measurement and detection involves applying an oscillatory magnetic field to the sample, preferably sinusoidally varying magnetic field, and lock-in detecting the output signal at the second harmonic of the frequency applied oscillatory magnetic field. The present apparatus will sometimes be referred to herein as the Magneto-Optical Phase Enantiomeric Detector or MOPED apparatus or system. The MOPED apparatus yields much more information than available with simple polarimetry, and also provide dramatically increased sensitivity and decreased analysis time.

The present invention provides a novel and powerful polarimetry apparatus, suitable for measurement of optical rotation and other related optical properties of a sample, with enhanced sensitivity, faster data acquisition, and higher throughput suitable for rapid screening of chiral compounds including chiral catalysts.

The present invention provides an apparatus including a sample cell, a polarized light source for supply polarized light to a sample in the cell, a magnetic field generator surrounding the cell for applying a time varying magnetic field to the sample in the cell, an analyzer for analyzing transmitted light passing through the sample, a detector for detecting the output of the analyzer and generating a sample detector output signal, a lock-in amplifier for receiving the detector output signal and generating an amplitude and a phase of the detector output signal and a power supply for supplying a time varying electrical input to the coil and for supply a reference input or lock input to the lock-in amplifier.

The present invention also provides an apparatus including a multi-compartment sample cell, a polarized light source for supply polarized light to a sample in each compartment of the cell, a magnetic field generator surrounding the cell for applying a time varying magnetic field to the samples in the cell, an analyzer for analyzing transmitted light passing through each sample in the cell, a detector for detecting each sample output from the analyzer and generating a sample detector output signal of each sample, a lock-in amplifier for receiving the detector output signal from each sample and generating an amplitude and a phase of the detector output signal for each sample and a power supply for supplying a time varying electrical input to the coil and for supply a reference input or lock input to the lock-in amplifier.

The present invention provides a method including the steps of transmitting polarized light through a sample cell containing a sample including a chiral analyte and applying an oscillatory magnetic field to the sample within the cell. The method also includes the steps of analyzing transmitted light to produce an analyzed signal, detecting the analyzed signal to produce an output signal and amplifying the signal locked to a signal used to produce the oscillatory magnetic field to produce an output signal amplitude and phase.

The present invention provides a method including the steps of transmitting polarized light through a cell having a plurality of sample compartments, each compartment containing a sample including a chiral analyte and applying an oscillatory magnetic field to the samples within each compartment of the cell. The method also includes the steps of analyzing transmitted light from each compartment to produce an analyzed signal from each sample, detecting the analyzed signal from each analyte to produce an output signal for each analyte and amplifying each analyte signal locked to a signal used to produce the oscillatory magnetic field to produce an output signal amplitude and phase for each analyte.

DESCRIPTION OF THE DRAWINGS

The invention can be better understood with reference to the following detailed description together with the appended illustrative drawings in which like elements are numbered the same:

FIGS. 7A-D depict signal waveforms that result from operating the MOPED of FIG. 6A under different conditions, where the large sinusoidal curve is applied external magnetic field vs. time, and other superimposed curve is the output light intensity: FIG. 7A depicts a constant output signal which result in the absence of the Faraday effect, even if chiral species are present in the sample; FIG. 7B depicts a linear Faraday effect induces sinusoidal output signal in the absence of chiral species; FIG. 7C depicts a phase-shifted output signal in the presence of both chirality and the Faraday effect; and FIG. 7D depicts a distorted output signal in the presence of higher-order Faraday effects where, detection at higher lock-in frequencies yields the higher-order terms;. The second-order Faraday term is a manifestation of the chirality and can be more sensitively detected than the simple chirality, which is subject to more sources of noise;

FIG. 8A depicts another preferred embodiment of a MOPED apparatus of this invention including a multi-chambered cell;

FIGS. 8B-D depict a preferred fiber optics light delivery system and associated multi-chambered sample cell and manifold for associated each optical fiber with its corresponding sample chamber;

FIG. 8E depicts another preferred embodiment of a multi-chambered sample cell of this invention;

FIGS. 10A&B depict another preferred embodiment of an optical fiber/first polarizer construction and an optical fiber/second polarizer construction, respectively; and FIGS. 10C&D depict another preferred embodiment of an optical fiber/second polarizer construction and an optical fiber/second polarizer construction, respectively.

DETAILED DESCRIPTION OF THE INVENTION

Figure 1:
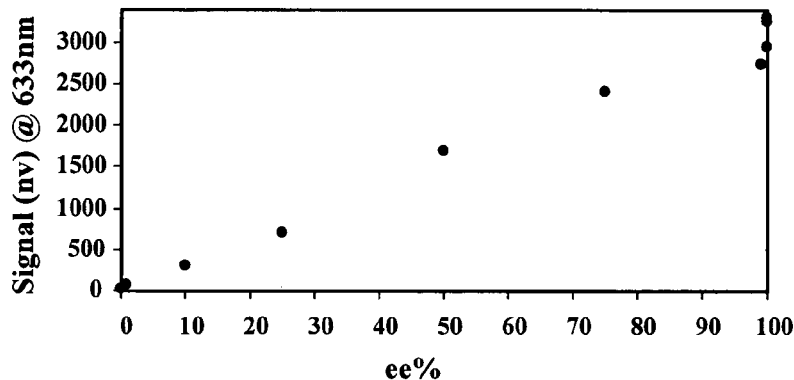
FIG. 1 depicts a plot of a detected lock-in signal (nv) versus Enantiomeric Excess (ee%) of S-(+)-Mandelic Acid (2 mg/mL)

The inventors have found that a new polarimetry apparatus and method using the apparatus can be constructed and implemented that greatly enhances sensitivity, lowers detection limits, decreases detection times, and increases sample throughput. The apparatus and method uses a polarized light source and a sample cell positioned within the interior of a magnetic field generator such as an Helmholtz coil or a solenoid. The generator is driven by a power supply so that the sample is exposed to an oscillatory magnetic field. The polarized light then interacts with chiral components in the sample. The resulting light is analyzed by a second polarizing substantially crossed relative to the first polarizer and amplified with lock-in amplification and optionally optical heterodyne detection which enhance a sensitive of a substance's chirality and lowers a detection limit for the substance or analyte in the sample. The oscillatory magnetic field (sample modulation) and the locked amplification allows more precise and accurate measurement optical rotation and of higher order harmonics (e.g, second harmonic, third harmonic, etc.) of magnetic field driving frequency and in turn a more precise and accurate measurement of an analytes chiral properties.

The present invention broadly relates to a method for detecting optical properties of an analyte in a sample including the steps of passing an incident polarized light beam having a defined bandwidth through a sample, where the sample is under the influence of a periodically varying magnetic field. The resulting light is then passed through an analyzer arranged substantially crossed with respect to the angle of polarization of the incident polarized light beam to reduce the resulting beams intensity, which is forwarded to a detector to produce an output signal. If the incident light beam is also modulated about the polarization angle, then an optical heterodyne detection system can be used as well, which takes advantage of a small amount of incident light to further enhance signal detection—the cross polarizer is slightly uncrossed or leaks. The output signal is then forwarded to a lock-in amplifier locked to the frequency of the magnetic field, higher harmonics thereof, the polarization modulation frequencies or mixtures or combinations thereof to produce an amplified Output having a magnitude and phase.

The present invention broadly relates to an apparatus for enhanced detection of optical properties of analytes, where the apparatus includes a light source adapted to generate a beam of light having a defined and/or narrow bandwidth, preferably, a well-defined and/or very narrow bandwidth, particularly, a bright light beam, preferably substantially monochromatic light or a combination of light from two or more monochromatic light sources, and most particularly, a light beam of a single frequency produced by a laser. The incident light beam is polarized by a first polarizer to a generate a polarized light beam. The polarized light beam is then directed into a sample cell including an analyte. The sample cell resides within a magnetic field generator adapted to generate a periodically varying magnetic field across the sample cell such that the analyte is exposed to a periodically varying magnetic field as the polarized light passes through the cell. The magnetic field results from a periodically varying applied electric current supplied by a power supply. The light exiting the cell is then forwarded to a second polarizer aligned substantially out-of-phase with the first polarizer to block substantially all of the incident polarized light from reaching a detector. The detector converts the analyzed beam into an output signal, which is forwarded to a lock-in amplifier which amplifies the signal and generates an amplitude and phase of the detected signal.

The present apparatus can also include a cell with multiple sample chambers with a light delivery system for providing substantially monochromatic light to each chamber and passing each light beam from each chamber to an analyzer and then to a multielement detector and lockin-amplifier or a combined multielement detector and lock-in amplifier such as a lock-in CCD. Narrow bandwidth for the purpose of this invention is defined as light center about a base frequency and having a frequency differing from the base frequency by less than about 1%, preferably, less than about 0.5% and particularly, less than about 0.1% and where the intensity of the light is centered about the base frequency and the light having a different frequency comprises less than about 1% of the total intensity of the beam, preferably, less than about 0.5%, aid particularly, less than about 0.1%. The term very narrow bandwidth for the purposes of this invention means substantially monochromatic light, where substantially means that less than about 1% of the light is not of a base frequency, preferably, less than about 0.5% and particularly, less than about 0.1%. The term monochromatic light means light of a single frequency. Although for many application of this invention, light having a narrow, defined bandwidth is preferred. For CD or other application, broad bandwidth light is preferably, especially when coupled with a multi-frequency detection system such as a lock-in CCD or a plurality of individual lock-in detectors.

The preferred apparatus and method of this invention for circular dichroism utilizes a broad set of wavelengths or if the adsorption spectrum of the analyte is known, a single wave length at or near the absorption maximum. The input light would comprise both forms of circularly polarized light in a time varying format, which can be accomplished by using a rotating quarter waveplate, a photo-elastic modulator (PEM), or other methods to time modulate the state of circularly polarized light inserted into the light beam prior to the first polarizer.

The present invention also relates to an apparatus using multiple frequencies lock-ins. A lock-in amplifier typically detects at the frequency of the reference signal. However, the principal of lock-in detection can be applied to signals present at more than one reference frequency such as higher multiples and multiples plus or minus another modulating frequency. All of these signals can be analyzed simultaneously and detecting identical terms such as the second order Faraday effect at more than one frequency provides a more robust signal detection scheme since the sources of noise at each detected frequencies tend to average out. It is particularly advantageous to detect multiple signals at a number of lock-in frequencies so that the number of equations exceeds the number of unknowns.

Introduction

There is an increasing need for drugs with enantiomerically pure active ingredients and for enantiomerically pure intermediates.[2] In fact, future drugs are likely to require active ingredients with ever increasing enantiomers or diastereomers purities. Biocatalysis has huge potential for the synthesis of such enantiomerically pure ingredients.[2] But efficient development of techniques capable of producing large number of candidate ingredient such as biocatalysts requires new high-throughput screening methodologies and apparatuses both for the discovery of environmental samples[64] or for the development of candidates using such preparation techniques as directed-evolution.[4] The present invention is well-suited as a high-throughput screening technique for such development efforts.

Combinatorial chemistry has fundamentally changed the process by which new drugs and materials are discovered. The combinatorial approach allows a researcher to generate up to millions of candidate compounds in days or weeks, as opposed to the traditional approach of creating and testing compounds sequentially (one at a time). Combinatorial chemistry coupled with the new high-throughput screening apparatus and methodology of this invention allowing desired candidates to be picked from a large library at a tremendously accelerates pace.

In the related field of biocatalysis, recent advances in directed evolution have enabled researchers to generate improved versions of existing enzymes by screening tens of thousands of novel mutant enzymes. One of the areas in which enzymatic catalysis excels is in the area of reaction that require high stereoselectivity and/or stereospecificity, whihc would greatly benefit many industrial processes. Since the occurrence of a beneficial mutation is a rare event[3], a high-throughput screening techniques such as that disclosed herein is essential to efficiently evaluate enough candidates from the gene-shuffling experiments to have a reasonable probability of finding an improved enzyme. Except for this invention, to date and despite tremendous advances in the combinatorial chemistry, a generally applicable high-throughput screening method for chiral compounds or stereoselective catalysts does not exist, the reports of some successful examples of screening using specially labeled substrates or alternative reporter systems notwithstanding[41,46].

Theory of Higher-order Magnetically Induced Optical Polarization Rotation in Chiral Simultaneously utilizing such techniques as a temporally sinusoidal magnetic field, higher-order Faraday effects (magnetic-field-induced polarization rotation with higher-order dependences on the magnetic field), harmonic lock-in detection (detecting at harmonics of the sinusoidally varying magnetic field), and optical heterodyne detection (detecting the interference term between a weak signal and strong input optical field) in combination should enhance sensitivity by more than an order of magnitude. But while the apparatus remains simple, the use of this sophisticated combination of techniques requires careful analysis. We must measure the lock-in signal vs. several input parameters: local-oscillator field, magnetic field, sample concentration and chirality, and harmonic order. The second-order Faraday effect is uniquely determined by a quadratic magnetic field dependence and may also be determined from a square-root dependence on the local-oscillator intensity of the second harmonic lock-in signal, for example. We expect to find that these methods will provide, not only an extremely sensitive overall concentration measure, but also considerably more information than simple optical rotation present in polarimetry. Thus this device should have much greater generality than polarimeters.

Theoretically, the system of this invention obeys the following set of equations which definge the electric field response to the oscillatory magnetic field B(t), the resulting frequency domain equation after Fourier transformation and simplification and the resulting responses that can be observed in theory.

Derivation of the Electric Field Intensity in the Sample (Time Domain)

The following equations represent the derivation of the intensity of the electric field experienced by a component of the sample during the influence of an oscillatory magnetic field:

$$Elo = Ein\theta$$

$$Esig = Ein(\alpha + \upsilon B(t) + \beta B(t)^2 + \Gamma B(t)^3)$$

$$B(t) = B\cos(\omega t)$$

$$Esig = Ein(\alpha + \upsilon B\cos(\omega t) + \beta B^2 \cos^2(\omega t) + \Gamma B^3 \cos^3(\omega t))$$

$$Efield = Elo + Esig$$

$$Efield = Ein\theta + Ein(\alpha + \upsilon B\cos(\omega t) + \beta B^2 \cos^2(\omega t) + \Gamma B^3 \cos^3(\omega t))$$

$$EFieldcj = Ein\theta + Ein(\alpha + \upsilon B\cos(\omega t) + \beta B^2 \cos^2(\omega t) + \Gamma B^3 \cos^3(\omega t))$$

$$\text{Intensity} = Efieldcj + Efield$$

-continued $$\text{Intensity} = Ein^2\theta^2 + Ein^2\alpha^2 + Ein^2\upsilon^2 B^2\cos^2(\omega t) +$$
$$Ein^2\beta^2 B^4\cos^4(\omega t) + Ein^2\Gamma^2 B^6\cos^6(\omega t) + 2Ein^2\theta\alpha +$$
$$2Ein^2\theta\upsilon B\cos(\omega t) + 2Ein^2\theta\beta B^2\cos^2(\omega t) +$$
$$2Ein^2\theta\Gamma B^3\cos^3(\omega t) + 2Ein^2\alpha\upsilon B\cos(\omega t) +$$
$$2Ein^2\alpha\beta B^2\cos^2(\omega t) + 2Ein^2\alpha\Gamma B^3\cos^3(\omega t) +$$
$$2Ein^2\upsilon\beta B^3\cos^3(\omega t) + 2Ein^2\upsilon\Gamma B^4\cos^4(\omega t) +$$
$$2Ein^2\beta\Gamma B^5\cos^5(\omega t)$$

Derivation of the Spectrum Equation After Fourier Transformation (Frequency Domain)

The following equations represent the spectrum corresponding to the intensity of the electric field experienced by a component of the sample during the influence of an oscillatory magnetic field derived above after Fourier transformation from the time domain to the frequency domain:

$$\text{Spectrum} = \left(2Ein^2\theta\beta B^2\pi + 2Ein^2\alpha\beta B^2\pi + 2Ein^2\theta^2\pi + Ein^2\upsilon^2 B^2\pi + \frac{3}{2}Ein^2\upsilon\Gamma B^4\pi + \frac{3}{4}Ein^2\beta^2 B^4\pi + 2Ein^2\alpha^2\pi + \frac{5}{8}Ein^2\Gamma^2 B^6\pi + 4Ein^2\theta\alpha\pi\right)\delta(w) +$$
$$\left(\frac{3}{2}Ein^2\theta\Gamma B^3\pi + \frac{3}{2}Ein^2\alpha\Gamma B^3\pi + \frac{5}{4}Ein^2\beta\Gamma B^5\pi + \frac{3}{2}Ein^2\upsilon\beta B^3\pi + 2Ein^2\alpha\upsilon B\pi + 2Ein^2\theta\upsilon\pi\right)\delta(w-\omega) +$$
$$\left(\frac{3}{2}Ein^2\theta\Gamma B^3\pi + \frac{3}{2}Ein^2\alpha\Gamma B^3\pi + \frac{5}{4}Ein^2\beta\Gamma B^5\pi + \frac{3}{2}Ein^2\upsilon\beta B^3\pi + 2Ein^2\alpha\upsilon B\pi + 2Ein^2\theta\upsilon\pi\right)\delta(w+\omega) +$$
$$\left(\frac{1}{2}Ein^2\upsilon^2 B^2\pi + \frac{15}{32}Ein^2\Gamma^2 B^6\pi + Ein^2\theta\beta B^2\pi + Ein^2\upsilon\Gamma B^4\pi + \frac{1}{2}Ein^2\beta^2 B^4\pi + Ein^2\alpha\beta B^2\pi\right)\delta(w-2\omega) +$$
$$\left(\frac{1}{2}Ein^2\upsilon^2 B^2\pi + \frac{15}{32}Ein^2\Gamma^2 B^6\pi + Ein^2\theta\beta B^2\pi + Ein^2\upsilon\Gamma B^4\pi + \frac{1}{2}Ein^2\beta^2 B^4\pi + Ein^2\alpha\beta B^2\pi\right)\delta(w+2\omega) +$$
$$\left(\frac{5}{8}Ein^2\beta\Gamma B^5\pi + \frac{1}{2}Ein^2\theta\Gamma B^3\pi + \frac{1}{2}Ein^2\alpha\Gamma B^3\pi + \frac{1}{2}Ein^2\upsilon\beta B^3\pi\right)\delta(w-3\omega) + \left(\frac{5}{8}Ein^2\beta\Gamma B^5\pi + \frac{1}{2}Ein^2\theta\Gamma B^3\pi + \frac{1}{2}Ein^2\alpha\Gamma B^3\pi + \frac{1}{2}Ein^2\upsilon\beta B^3\pi\right)\delta(w+3\omega) +$$
$$\left(\frac{3}{16}Ein^2\Gamma^2 B^6\pi + \frac{1}{4}Ein^2\upsilon\Gamma B^4\pi + \frac{1}{8}Ein^2\beta^2 B^4\pi\right)\delta(w-4\omega) + \left(\frac{3}{16}Ein^2\Gamma^2 B^6\pi + \frac{1}{4}Ein^2\upsilon\Gamma B^4\pi + \frac{1}{8}Ein^2\beta^2 B^4\pi\right)\delta(w+4\omega) + \left(\frac{1}{8}Ein^2\beta\Gamma B^5\pi\right)\delta(w-5\omega) +$$
$$\left(\frac{1}{8}Ein^2\beta\Gamma B^5\pi\right)\delta(w+5\omega) + \left(\frac{1}{32}Ein^2\Gamma^2 B^6\pi\right)\delta(w-6\omega) + \left(\frac{1}{32}Ein^2\Gamma^2 B^6\pi\right)\delta(w+6\omega)$$

In using these equations to analyze experimental results or to determine the response to a system under different imposed experimental conditions, at least five different experimental conditions are capable of being detected and treated to obtain useful analytical data. The first conditions involves data derived from a sample undergoing sample modulation only, i.e., the sample is under the influence of an oscillatory magnetic field at a given and known frequency. The response is shown below:

Detector Response Base Case—Sample Modulation Only DC $$ResponseDC = \left(2\theta\beta B^2 + 2\alpha\beta B^2 + 2\theta^2 + \upsilon^2 B^2 + \frac{3}{2}\upsilon\Gamma B^4 + \frac{3}{4}\beta^2 B^4 + 2\alpha^2 + \frac{5}{8}\Gamma^2 B^6 + 4\theta\alpha\right)Ein^2\pi A_{eff}\text{Responsivity}(\lambda)R_{load}$$

First Harmonic (H1)

$$ResponseH1 = \left(\frac{3}{2}\theta\Gamma B^3 + \frac{3}{2}\alpha\Gamma B^3 + \frac{5}{4}\beta\Gamma B^5 + \frac{3}{2}\upsilon\beta B^3 + 2\alpha\upsilon B + 2\theta\upsilon\right)Ein^2\pi A_{eff}\text{Responsivity}(\lambda)R_{load}$$

Second Harmonic (H2)

$$ResponseH2 = \left(\frac{1}{2}\upsilon^2 B^2 + \frac{15}{32}\Gamma^2 B^6 + \theta\beta B^2 + \upsilon\beta B^3 + 2\alpha\upsilon B + 2\theta\upsilon\right)Ein^2\pi A_{eff}\text{Responsivity}(\lambda)R_{load}$$

Third Harmonic (H3)

$$ResponseH3 = \left(\frac{5}{8}\beta\Gamma B^5 + \frac{1}{2}\theta\Gamma B^3 + \frac{1}{2}\alpha\Gamma B^3 + \frac{1}{2}\upsilon\beta B^3\right)Ein^2\pi A_{eff}\text{Responsivity}(\lambda)R_{load}$$

Fourth Harmonic (H4)

$$ResponseH4 = \left(\frac{3}{16}\Gamma^2 B^6 + \frac{1}{4}\upsilon\Gamma B^4 + \frac{1}{8}\beta^2 B^4\right)Ein^2\pi A_{eff}\text{Responsivity}(\lambda)R_{load}$$

Fifth Harmonic (H5)

$$ResponseH5 = \left(\frac{1}{8}\beta\Gamma B^5\right) Ein^2 \pi A_{eff} Responsivity(\lambda) R_{load}$$

Sixth Harmonic (H6)

$$ResponseH6 = \left(\frac{1}{32}\Gamma^2 B^6\right) Ein^2 \pi A_{eff} Responsivity(\lambda) R_{load}$$

In this situation, there are six unknowns ($\alpha$, $\beta$, $\upsilon$, $\Gamma$, $\theta$ and Ein) and seven equations. From these equations, it is also apparent that the $\theta$ dependence occurs in the DC response, in the first harmonic (H1) response, in the second harmonic (H2) response and in the third harmonic (H3) response. The $\theta$ dependent terms are $2\theta\beta B^2+2\theta^2+4\theta\alpha$, $\frac{3}{2}\theta\Gamma B^3+2\theta\upsilon B$, $\theta\beta B^2$, and $\frac{1}{2}\theta\Gamma B^3$, respectively.

Detector Response—Sample and Light Modulation

The second situation involves sample modulation and polarization modulation of the incident polarized light beam, where the polarization is being modulated about $\theta$ with the function $\cos(\phi t)$. It this situation, the controlling independent equations are set forth below:

DC $$\left(2\alpha\beta B^2 + \upsilon^2 B^2 + \frac{3}{2}\upsilon\Gamma B^4 + \frac{3}{4}\beta^2 B^4 + 2\alpha^2 + \frac{5}{8}\Gamma^2 B^6\right)$$
$$Ein^2 \pi A_{eff} Resp(\lambda) R_{load}$$
$$[+\phi t](2\theta\beta B^2 + 4\theta\alpha) Ein^2 \pi A_{eff} Resp(\lambda) R_{load}$$
$$[+2\phi t]\left(\frac{1}{2}\theta^2\right) E_{in}^2 \pi A_{eff} Resp(\lambda) R_{load}$$

First Harmonic (H1)

$(\frac{3}{2}\alpha\Gamma B^3+\frac{5}{4}\beta\Gamma B^5+\frac{3}{2}\upsilon\beta B^3+2\alpha\upsilon B)Ein^2\pi A_{eff}Resp(\lambda)$
$R_{load} [\pm\phi t](\frac{3}{2}\theta\Gamma B^3+2\theta\upsilon B)Ein^2\pi A_{eff}Resp(\lambda)R_{load}$ Second Harmonic (H2)

$(\frac{1}{2}\upsilon^2B^2+\frac{15}{32}\Gamma^2B^6+\upsilon\Gamma B^4+\frac{1}{2}\beta^2B^4+\alpha\beta B^2)$
$Ein^2A_{eff}Resp(\lambda)R_{load}[\pm\phi t](\theta\beta B^2)Ein^2\pi A_{eff}Resp$
$(\lambda)R_{load}$ Third Harmonic (H3)

$(\frac{5}{8}\beta B^5+\frac{1}{2}\alpha\Gamma B^3+\frac{1}{2}\upsilon\beta B^3)Ein^2\pi A_{eff}Resp(\lambda)R_{load} [\pm\phi t]$
$(\frac{1}{2}\theta\Gamma B^3)Ein^2\pi A_{eff}Resp(\lambda)R_{load}$ From these equations, it is apparent that there are again six unknowns ($\alpha$, $\upsilon$, $\beta$, $\Gamma$, $\theta$, and Ein) and eleven equations from which to determine them.

In the third situation, the sample is not under the influence of an oscillating magnetic field, but under the influence of a polarization light source which is being oscillated about a value $\theta$ by the function $\cos(\phi t)$ or a situation where $\beta$ and $\Gamma$ are below Detection Limit of the detector giving rise to the equation representing the response as shown below:

Detector Response—$\beta$ and $\Gamma$ below Detection Limit

DC $(\upsilon^2B^2 + 2\alpha^2)Ein^2\pi A_{eff}Resp(\lambda)R_{load}$
$[+\phi t](4\theta\alpha)Ein^2\pi A_{eff}Resp(\lambda)R_{load}$
$[+2\phi t]\left(\frac{1}{2}\theta^2\right)E_{in}^2\pi A_{eff}Resp(\lambda)R_{load}$ First Harmonic (H1)

$(2\alpha\upsilon B)Ein^2\pi A_{eff}Resp(\lambda)R_{load}[\pm\phi t](2\theta\upsilon B)$
$Ein^2\pi A_{eff}Resp(\lambda)R_{load}$ Second Harmonic (H2)

$(\frac{1}{2}\upsilon^2B^2)Ein^2\pi A_{eff}Resp(\lambda)R_{load}$

Third Harmonic (H3)
No contribution.

From these equations, it is apparent that there are again four unknowns ($\alpha$, $\upsilon$, $\theta$, and $E_{in}$) and six equations from which to determine them. It is also apparent from these equations that the DC term is not of much use.

In the forth situation, the sample is being analyzed only for achiral species so that the chiral species signals can be determined from difference spectral analysis; the controlling equation are listed below:

Detector Response—Achiral Species (Solvent $\alpha=\beta=\Gamma=0$)

DC $(\upsilon^2B^2)Ein^2\pi A_{eff}Resp(\lambda)R_{load}[+2\phi t](\frac{1}{2}\theta^2)$
$E_{in}^2\pi A_{eff}Resp(\lambda)R_{load}$ First Harmonic (H1)

$[\pm\phi t](2\theta\upsilon B)Ein^2\pi A_{eff}Resp(\lambda)R_{load}$

Second Harmonic (H2)

$(\frac{1}{2}\upsilon^2B^2)Ein^2\pi A_{eff}Resp(\lambda)R_{load}$

Third Harmonic (H3)
No contribution.

From these equations, it is apparent that there are again three unknowns ($\upsilon$, $\theta$, and Ein) and four equations from which to determine them.

In the third situation, the sample is not under the influence of an oscillating magnetic field, but under the influence of a polarization light source which is being oscillated about a value $\theta$ by the function $\cos(\phi t)$ or a situation where $\beta$ and $\Gamma$ are below Detection Limit of the detector giving rise to the equation representing the response as shown below:

Detector Response—Light Modulation Only

DC $[+\phi t](4\theta\alpha)E_{in}^2\pi A_{eff}Resp(\lambda)R_{load}[+2\phi t](\frac{1}{2}\theta^2)$
$E_{in}^2\pi A_{eff}Resp(\lambda)R_{load}$ First Harmonic (H1)
No contribution.
Second Harmonic (H2)
No contribution.

Third Harmonic (H3)

No contribution.

From these equations, it is apparent that there are again three unknowns ($\alpha$, $\theta$, and $E_{in}$), but now two equations from which to determine them. Therefore, a separate measurement of $E_{in}$ will have to be measured to fully describe the system.

From the above derivation, the gamma and beta terms are due only to contributions from chiral components and not from non-chiral components. Thus, a determination of gamma and beta allow determination of contributions from chiral components free of contamination of non-chiral components.

Circular Dichroism

The physical principles involved in the detection of optical rotation in MOPED systems of this invention can also be used to determine the compounds possessing circular dichroism (CD)[67]. The required change in apparatus is quite simple. The change requires insertion of a quarter wave plate into the apparatus between the light source and the first polarizer. In addition, a lock-in CCD camera allows CD spectrum determination in a manner analogous to diode-array spectrophotometers greatly improving the speed of analysis, which utilizes a diffraction grating to analyze the separate wavelengths. Extension of the MOPED apparatus to CD detection allows routine investigation of phenomena such as protein secondary structure in a rapid manner currently unavailable to most researchers. While lock-in CCD cameras are currently under development, the relevant techniques and instrumentation can be developed by investigating wavelengths scanned over spectral range of interest.

Rapid Optical Rotation Measurement for High Throughput Analytical Screening

The high-throughput capability of the MOPED of this invention is based on the rapid detection capability of lock-in amplifiers. Generally, the system is capable of measuring many samples per minute, and preferably one sample per sample and particularly, one sample in under one second. These speeds are especially geared toward multi-chambered cells and/or 96-well plates or and 384-well plates. Using lock-in CCD cameras, the system can detect optical rotation and other optical properties in the respective well plates or individual chambers. This multi-element detector allows multiple wavelengths to be examined and/or multiple sample wells to be analyzed in parallel, while simultaneously providing all of the advantages of lock-in detection for each detector element. Besides a CCD camera, the present invention can use a plurality or an array of individual detectors and lock-in amplifiers to measure different spectral frequencies and/or different samples simultaneously.

Benefits of the Apparatus and Methods of this Invention

While some progress in laser-based polarimetry has been achieved in the past few years, the apparatus of this invention includes several novel and innovative features: (1) the use of harmonic lock-in detection in conjunction with applying an oscillating magnetic field to the sample, preferably, a sinusoidally varying magnetic field, (2) the use of the second-order Faraday effect to improve analysis sensitivity, (3) the use of optical heterodyne detection, and (4) the use of a lock-in CCD camera. The combination of these features allows the apparatus and methods of this invention to achieve high-throughput, a necessary features of any technique for screening compounds generated by any of the newer generation techniques.

The apparatuses and methods of this invention address at least three shortfalls of current polarimetry: (1) a sensitivity cap of about 1 millidegree, (2) a throughput based on single sample processing, (3) a limitation to simple optical rotation measurements, and (4) a limitation on measuring a total concentration of enantiomers or optically active species. The present invention can precisely and accurately measure simple optical rotation, but also provides measurements of other reliable optical properties and parameters, and offers improvements in measuring total concentration of the enantiomers or optically active species in addition. The present invention can screen multiple sample simultaneously. The present invention can accomplished these improvement using a standard cuvette having a 1 cm path-length. Moreover, the present invention offers sensitivity at least one order of magnitude higher than traditional polarimetry and measurement of total enantiomers much better than traditional polarimetry.

Polarimetry has not progressed much in recent decades. The last modification realizing an order of magnitude improvement for a general-purpose analytical polarimeter was the introduction of a Faraday isolator by Gillham in 1957[26,27]. The present invention relates to a simple, reliable laser optics-based, high-throughput polarimeter ideally suited for use in the drug-development community, by adapting recent advances in laser optics, to the analytical problem of screening samples including chiral species.

History of Chirality

Anisotropic crystalline solids and samples containing an excess of one enantiomer of a chiral molecule rotate a plane of polarization of plane-polarized light. This phenomenon was first discovered by the French physicist Jean-Baptiste Biot in his studies on quartz crystals. Subsequently, Louis Pasteur, a student of Biot, made a series of more famous observations involving solutions of tartaric acid from the tartar deposits in maturing barrels of wine[43]. In this seminal work, Pasteur noted that two crystalline forms were observed of the sodium-ammonium double salt of para-tartaric acid, also called racemic acid (from the Latin racemus, a bunch of grapes). He manually separated these crystals and noted that the separate solutions, with equivalent concentrations of tartaric acid crystals, rotated linearly polarized light in equal but opposite directions. From this observation, Pasteur inferred that optically inactive racemic acid was composed of equal amounts of (+) and (−) tartaric acid. Thereafter, the term racemate was used to describe an optically inactive equimolar mixture of optical isomers[51]. Interestingly, Faraday made his first observation of the magnetically induced rotation effect that bears his name several years earlier in 1846 and Pasteur following on his epochal discovery in 1848 tried in vain to induce chirality by growing crystals in magnetic fields[17]. Lord Kelvin, who is attributed with introducing the word "chirality" (from the Latin chiro, meaning hand) into science, noted that the magnetic rotation was not the source of chirality[36].

Optical isomers, more commonly called enantiomers, are important in several fields, including pharmacology, chemistry, and the study of essential oils, flavor, and food industries. The science of measuring of this change in polarization orientation is called polarimetry, and the measuring instrument is called a polarimeter. These measurements are useful for studying the structure of anisotropic materials, and for checking the purity of chiral mixtures or chiral compounds.

A sample containing an equimolar mixture of enantiomers is called a racemate, as described previously, and a sample that contains only one enantiomer of a chiral molecule is said to be optically pure. The enantiomer that rotates light to the left, or counterclockwise, is called the levorotatory (l) or (−) enantiomer, and the enantiomer that rotates light to the right, or clockwise when viewing in the direction of light propagation, is called the dextrorotatory (d) or (+) enantiomer.

The phenomenon of optical rotation occurs because optically active samples have different refractive indices for left- and right-circularly polarized light. Stated differently, the left- and right-circularly polarized light travel through an optically active sample at different velocities. This condition occurs because a chiral center has a specific geometric arrangement of four different substituents, each of which has a different electronic polarizability. Interactions occur between the light traveling through the medium and the electron clouds that are present in the compounds interacting with the light. Left-circularly polarized light, therefore, interacts with an anisotropic medium differently than does right-circularly polarized light.

Linearly or plane-polarized light can be represented as the superposition of equal intensities of left- and right-circularly polarized light. As plane-polarized light travels through an optically active sample, the left- and right-circularly polarized components travel at different velocities. This difference in velocities creates a phase shift between the two circularly polarized components when they exit the sample. The summation of the two components still produces linearly polarized light, but at a different orientation from the light entering the sample.

Polarimetry

In developing enantiomerically pure drugs, optical purity must be measured and/or achieved at many stages in the synthetic process. This requirement leads to a large demand for measurements of optical activity; these measurements are usually made by chiral high-performance liquid chromatography[5], Circular Dichroism, or by polarimetry. The molecular structure and concentration of chiral molecules in the samples determine the amount of optical rotation. Each optically active substance has its own specific rotation as defined by Biot's law:

$$\alpha_\lambda^T = c \cdot l \cdot [\alpha]_\lambda^T$$

where a $[\alpha]_\lambda^T$ is the specific rotation at a specified temperature, T, and wavelength λ. The concentration, c, is given in g/mL and optical path length, l, is given in dm. The observed optical rotation is $\alpha_\lambda^T$. Historically, polarimetry has been performed at 589 nm, the sodium D-line, and most literature values are reported at this wavelength. This was largely due to sodium lamps being a bright monochromatic light source. However, modern instruments contain improved light sources and are not restricted to measurements of optical rotation at 589 nm. In fact, modern polarimeters, coupled with a monochromator are capable of obtaining optical rotation over a range of wavelengths, and are known as spectropolarimeters. The reported specific rotations of samples are assumed to have a 1 dm path length by convention, unless otherwise stated. However, the concentration and solvent conditions of reported specific rotations are arbitrary and must be checked to avoid errors.

Optical purity is defined by the following relation:

$$\text{Optical purity} = \frac{[\alpha]}{[\alpha]_0} \times 100\%$$

where [α] is the optical rotation of the mixture and $[\alpha]_0$ is the specific rotation of the pure enantiomer. However, the term optical purity is not generally used, since solutions of different chemical purities cannot be directly compared. Due to this ambiguity, the unambiguous term of enantiomeric excess has supplanted the term optical purity. The definition of enantiomeric excess, for which R>S, is shown in the equation below[51]. The R/S nomenclature is based on the determination of priority of the substituents on a carbon atom by the Prelog rules but does not give any information on the preferred rotation of the compounds to which they are assigned. As an example of computing the enatiomeric excess (ee), a sample containing S and R enantiomers in a ratio of 80:20 has an ee of 60% for the S enantiomer.

$$ee = \frac{(S-R)}{(S+R)} \times 100\%$$

Using these relations, polarimetry is employed in quality testing, process control, and research in the pharmaceutical, chemical, essential oil, flavor, and food industries. It is so well established that the United States Pharmacopoeia and the Food & Drug Administration gives polarimetric specifications for numerous substances[55].

Traditional Polarimeter

The earliest instrument employed by Biot around 1816[63], called a polariscope, used a prism to produce a beam of plane-polarized light, generally at the sodium D line, which then passed through a sample tube, after which it was analyzed using a second Nicol prism polarizer with a circular scale. In order to improve the readability and accuracy of the instrument, another Nicol prism polarizer was placed in front of the polarizer to create a split field by introducing a few degree of rotation for half of the light. The instrument was then adjusted to match the two halves of the resulting field by visual inspection. The angle adjustment needed to match the fields is read as the overall optical rotation[30]. A modern version of this device has an accuracy of about 0.1 degrees.

The advent of electronics advanced the design of the polarimeter by replacing visual inspection with direct photon detection using a photon detector. The analyzer, a second polarizer, is substantially crossed relative to the polarized monochromatic light passing through the first polarizer from the source. The analyzer is used to minimize light reaching the detector. When an optically active solution is then placed between polarizer and analyzer, the light flux seen at the detector increases. The electronics rotate the analyzer to compensate for this increase, reminimizing the light flux to the detector. The angle that the analyzer must be rotated to return to the minimum is the optical rotation, a. A simple polarimeter of this type has an accuracy of about 0.01 degrees or 10 millidegrees[52].

The accuracy of the polarimeter was greatly improved by the introduction of a Faraday compensator[26]. This element introduces a modulation to the linearly polarized beam, preferably, before the beam passed through the sample[18]. By modulating the beam angle larger than the maximum error angle, this effectively linearizes the input-output relation and allows the resolution of extremely small angle error. Modern devices based on this design have an angle resolutions of about 0.001 degrees or 1 millidegree.

Traditional polarimeters require large sample volumes, solutes at relatively high concentrations, and can take several minutes to achieve a stable reading. All of these requirements are inconvenient for chiral analysis and are impractical for the analysis of high throughput compound generating techniques such as combinatorial chemistry and the like, where small samples volumes and rapid analysis are required.

More recent advances in polarimetry have included a laser-based polarimeter for chiral detection on HPLC systems[16]. These systems have reported accuracies of 25 microdegrees, which is forty-fold greater than traditional polarimeters, and have sample chambers of only 22 µL. By improving the sensitivity and sample size, these detectors are finding applications in chiral detection where traditional polarimeters were inadequate. However, even with these advances, the current state-of-the-art laser polarimeter is a serial analysis technique, only determines optical rotation and not concentration, which would have to be determined separately and inadequately addresses the need for a broadly applicable high throughput chiral screen.

Circular Dichroism (CD)

Circular dichroism (CD) is the differential absorption ($\Delta\epsilon$) exhibited by a system for left- versus right-circularly polarized light. To demonstrate CD activity, a system must contain a dissymmetric center that is coupled in some manner to the chromophore which gives rise to the absorption, and thus, the term $\Delta\epsilon$ must be non-zero:

$$\Delta\epsilon = \epsilon_l - \epsilon_r \neq 0$$

In optical rotatory dispersion (ORD)[42], the effect forming the basis for polarimetry, the difference in refractive index ($\Delta\eta$) for left- versus right-circularly polarized light exhibited by an optically active system is measured. A molecule with a dissymmetric center is necessary for ORD activity, i.e., $\Delta\eta$ must be non-zero:

$$\Delta\eta = \eta_l - \eta_r \neq 0$$

Since the refractive index of a compound changes very slowly as a function of wavelength, except in the spectral region of an allowed transition, single wavelength optical activity measurements are frequently used. This mode is termed polarimetry.

One advantage polarimetry offers over circular dichroism for screening of chiral molecules or catalysts is one of universality. The presence of a chromophore and a chiral asymmetric center in a molecule is not sufficient for CD activity. The two moieties must be in intimate electronic contact for the absorbing center to be CD active. This dual requirement means that not all optically active compounds will exhibit a CD signal. A polarimetric response only requires that a molecule possess an asymmetric center. Polarimetric detection provides a response for virtually all chiral molecules, and is therefore more universal than detection by circular dichroism.

Other Chiral Detection Techniques

Several other techniques exist in addition to polarimetry and circular dichroism for the determination of enantiomeric purity. Conventional analysis techniques, coupled with a chiral stationary phase or product derivatization with an achiral stationary phase, such as HPLC[37] and gas chromatography (GC)[1] are the most common, but examples using capillary electrophoresis (CE) also exist[11]. While these techniques excel in the determination of enantiomeric excess once a method is established, not all compounds of interest have a suitable chiral stationary phase readily available, and some compounds are not readily derivatized for use on achiral stationary phases. Use of chiral detectors, laser-polarimetric[35] and circular dichroism[47], coupled with chromatographic separation, partially addresses these concerns, allowing the use of an achiral stationary phase without derivatization of the substrate. However, these techniques remain inherently serial methods and hence are limited to tens of samples per hour.

Recent Advances in High Throughput Screening

Given the increasing need for rapid analysis in the large libraries necessary for most combinatorial and directed evolution efforts, considerable research has been invested in the development of reliable high-throughput screening methods. The scope of these various screening technologies is too large for in-depth discussion here, but has been well reviewed in several recent articles[64,23,32,58,34]. However, the number of screening technologies developed for the problem of enantioselectivity is much more limited. One recent example used pH indicators to assay for the conversion of L- or D-methionine in a directed evolution effort to invert the selectivity of a wild type enzyme by directed evolution[41]. This assay required both substrates to be assayed separately and the results compared for the desired activity. While this effort was successful in finding a mutant enzyme with inverted enantioselectivity, approximately 10,000 clones were analyzed at each round with considerable manual effort. Similar approaches using both enantiomerically pure substrates have been used in other screening efforts including petri-plate approaches. However, enantiomerically pure substrates are not always available, and when they are, the associated cost is generally too high for large screening efforts by most researchers.

Alternatively, several researchers have tried to adapt HPLC, GC, and CE techniques mentioned above, in addition to mass-spectroscopy to conduct high-throughput screening. However, given the inherent serial nature of the analysis, a typically optimized HPLC or GC analysis can perform up to 1000 samples/day with a modified CE apparatus achieving approximately 7,000/day[46]. High throughput mass-spectrometry has also been investigated on deuterium labeled substrates with a typical throughput of 1000 samples/day.

Imaging methods provide the opportunity to increase analysis by enabling one to assay many samples in parallel[64,23]. Chromogenic dye assays and clearing zones around microbial colonies are two techniques that lend themselves to imaging analysis[15]. One company has further developed this technology to provide kinetic information on enzyme reactions occurring at each microcolony[10]. Thermal imaging has also been applied to enantioselective reactions where heats of reaction can indicate active enzymes[46]. However, these techniques also lack selectivity requiring the pure enantiomer to be supplied in two separate reactions. Imaging polarimetry was investigated for enzyme screening[24,25,66] but ultimately the sensitivity of the technique (0.05 degrees) was deemed too limited to be of value.

While advances certainly have been made in polarimetry and in the development of high throughput screening technologies, the present invention represents a marked improvement in the use of a relatively simple and flexible technique for detecting chiral compounds in samples in times of one second or less and allowing not only the optical rotation to be determine within this time, but also the enantiomeric excess (ee). Thus, the technique can be used to screen tens of thousands of samples sequentially in an eight hour day, and even higher through puts using parallel sample processing.

Experiments and Examples

Linear Faraday Effect with Enantiomers of Mandelic Acid

A first generation apparatus was constructed with existing lab equipment and a purchased Helmholtz coil and power supply and a series of tests were conducted to match experimental results to theoretical predicted results. The apparatus use a He—Ne laser generating monochromatic light at a wavelength of 633 nm was in conjunction with a Glan Thompson Calcite polarizer having a measured extinction coefficient of $10^{-6}$. The devices also used a Stanford Research Systems lock-in detector for signal analysis.

The enantiomers of mandelic acid were chosen for initial testing, because both enantiomers are commercially available in addition to the racemate. In addition, to being inexpensive, mandelic acid is also a versatile intermediate in the pharmaceutical industry[28]. Accurate preparation of standards to test for enantiomeric purity is non-trivial; moreover, the two commercially available enantiomers of mandelic acid have a reported ee of 99+%, but likely contain traces of the opposite enantiomer. Therefore, in order to obtain accurate standards to test in the apparatus, two solutions of equal concentration (2 mg/mL) were prepared from racemic mandelic acid and S-mandelic acid. Large volumes (100 mL) were prepared to ensure accurate compound weighing. Since the optical rotation of the racemate is known to be exactly zero and small volumes can be accurately and precisely measured with modern pipetors, volumes of each solution were mixed in order to achieve the desired enantiomeric ratios with the commercially supplied S-mandelic acid set as having an ee of 100%. Therefore, small ee standards were made with a high degree of confidence, even though the ultimate purity of the S-mandelic acid is unknown.

The Helmholtz coil was driven at a frequency of 800 Hz and the time constant on the lock-in was set at 10 seconds. At least one and half minutes were allowed to elapse (approximately, ten times the lockin-in time constant) before a instrument reading was taken. A 1-cm path-length quartz cuvette was used for holding the sample inside the Helmholtz coil. The results are shown in FIG. 1. The linear effect of the first order Verdet constant is clearly evident. Although this experiment used a time constant of 10 seconds, times constants of 100 millisecond or less are achievable with the apparatus of this invention.

Observation of Second-order Faraday Effect

Figure 2:
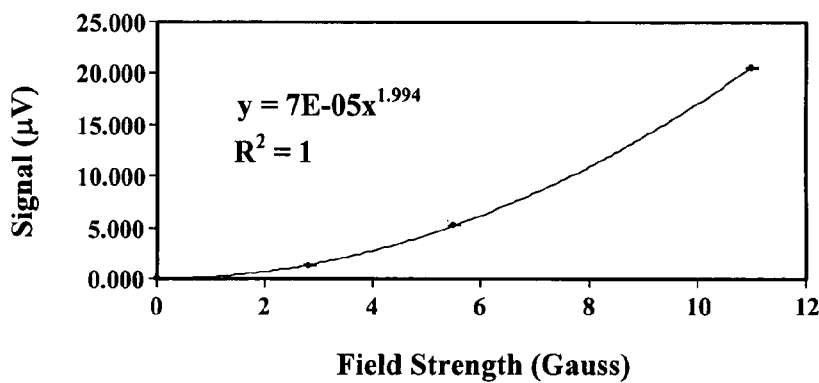
FIG. 2 depicts a plot of S-mandelate (20 mg/mL) Signal ($\mu$V) vs. Magnetic Field Strength Detected at 2$\omega$(532 nm, 200 mW, −0.025 millidegrees polarizer setting from null)
Figure 3:
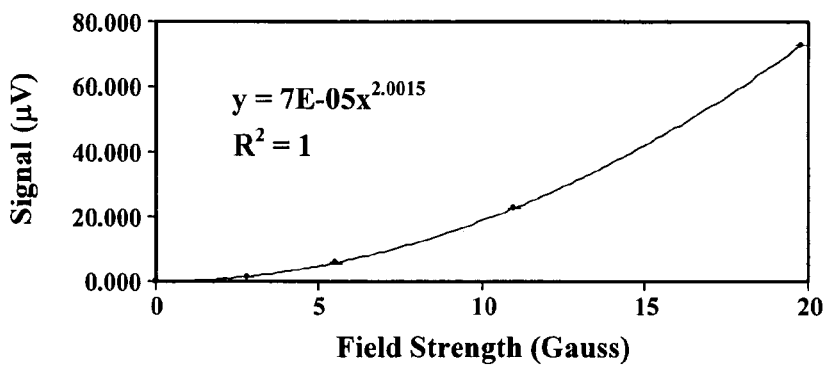
FIG. 3 depicts a plot of R-mandelate (20 mg/mL) Signal ($\mu$V) vs. Magnetic Field Strength Detected at 2$\omega$(532 nm, 200 mW, +0.025 milliDegrees polarizer setting from null)

Utilizing the Helmholtz coil, power supply set to 800 mHz, lock-in detector set for detection at 2 $\omega$, and a Verdi laser source at 532 nm 200 mW with the polarizers set to +0.0025 millidegrees measurements from the null point were made on both enantiomers of mandelic acid. As FIGS. 2 and 3 clearly demonstrate, there is a $B^2$ dependence of the detected signal. In addition, the leakage setting was equal but opposite in sign for the two enantiomers. Duplicate readings were made for the data and an error of only ±60 nv was observed (error bars plotted in FIGS. 2 and 3) which was attributed to difficulties in precisely resetting the power supply to the previous power setting due to knob inaccuracies on the power supply.

Second-order Faraday Effect for Analysis of Enantiomeric Purity

Figure 4:
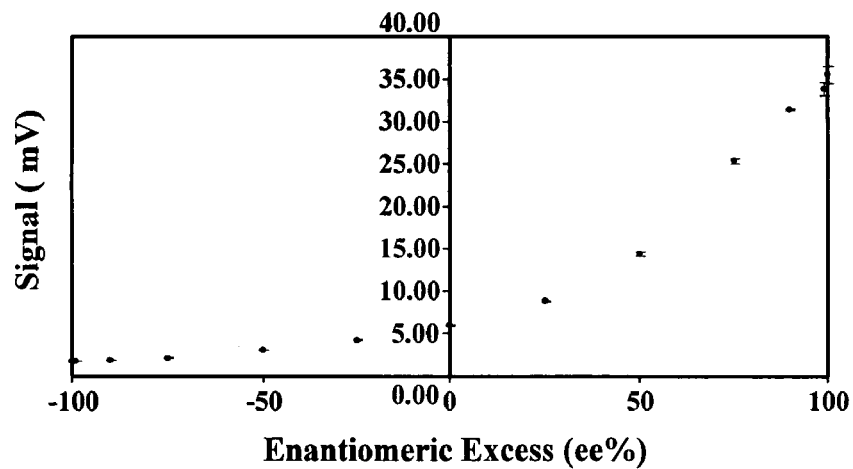
FIG. 4 depicts a plot of Mandelic Acid (10 mg/mL) at Different Enantiomeric Ratios (532 nm, 200 mW, −0.014 milliDegrees polarizer setting from null, 14.5 Gauss)
Figure 5:
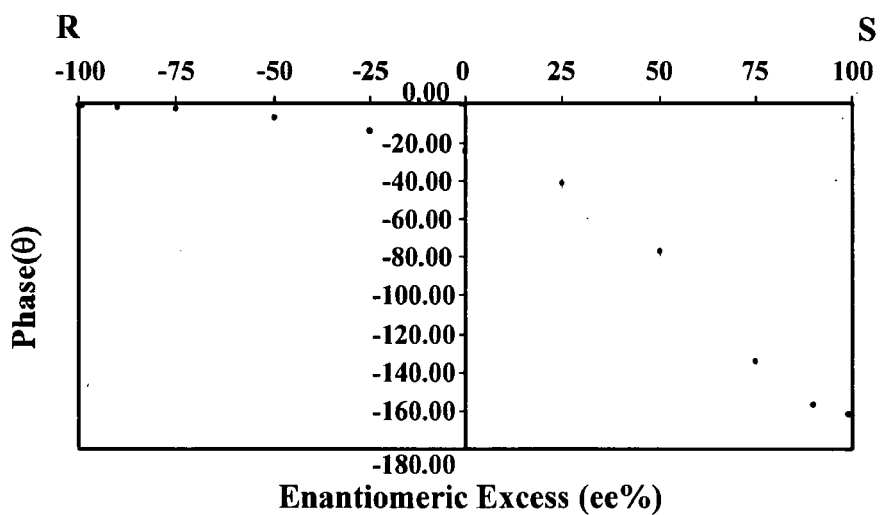
FIG. 5 depicts a plot of Mandelic Acid (10 mg/mL) at Different Enantiomeric Ratios (532 nm, 200 mW, −0.014 milliDegrees polarizer setting from null, 14.5 Gauss)

Once the observed $B^2$ signal dependence confirmed that the second-order Faraday effect is readily detectable, samples of mandelic acid at varying enantiomeric ratios but constant total concentration (10 mg/mL) were prepared as previously described and detected with the lock-in set to 2 $\omega$. The field was set to just below the maximum setting (750 mA) that the current Helmholtz coil could tolerate without cooling. FIG. 4 shows that these different mixtures are clearly differentiated even at these non-optimized settings. All samples were tested in triplicate. After sample testing the cell was removed and the liquid was replaced, washed at least 3 times with deionized water (DI), then at least 3 time washes with a new sample and then the new sample was loaded into the cell, before the next reading was performed. The apparatus was capable of distinguishing between a 100% ee R-mandelate (−) sample and a 99% ee R-mandelate (−) sample with observed signals of 1.78±0.01 µV and 1.80±0.01 µV, respectively. The apparatus was also capable of distinguishing between a 100%ee S-mandelate (+) sample and a 99%ee S-mandelate (+) sample with observed signals of 33.87±0.76 µV and 35.53±1.0 µV, respectively. At 532 nm the measured rotation of 10 mg/mL S-mandelate was 1.94 degrees and 1.53 degrees at 589 nm over a 10 cm path length in a Jasco P-1010. So a 1% ee difference at this concentration corresponds to less than 2.0 millidegrees rotation over the 1 cm path length (very close to the best available analytical polarimeters which have a detection limit of ±1 millidegree). In addition to the raw signal, phase information was also determined as shown in FIG. 5. The maximum observed error in this measurement was 2.3 degrees occurring at +25% ee (error bars are hard to observe due to their small size but are plotted on all points).

Design and Methods

Magneto-Optical Phase Enantiomeric Detector (MOPED)

Although traditional polarimeter could include beam-expanding telescopes placed between calcite polarizers to improve performance, such additional optical components sacrifice sensitivity. Thus, traditional polarimeters cannot be improved by the simple addition of optical devices. The apparatus of this invention provide a significant increase in the capability of polarimetry without the need for additional optical components in the light path.

The present invention using methods from field of non-linear laser spectroscopy, and applies these methods to polarimetry to produce a new generation of improved polarimetry instruments, without the addition of optical components. The new generation polarmetry instruments take advantage of detecting higher-order Faraday effects, which is a manifestation of a substance's chirality[61,59,69,60,67].

Figures 6A, 6B:
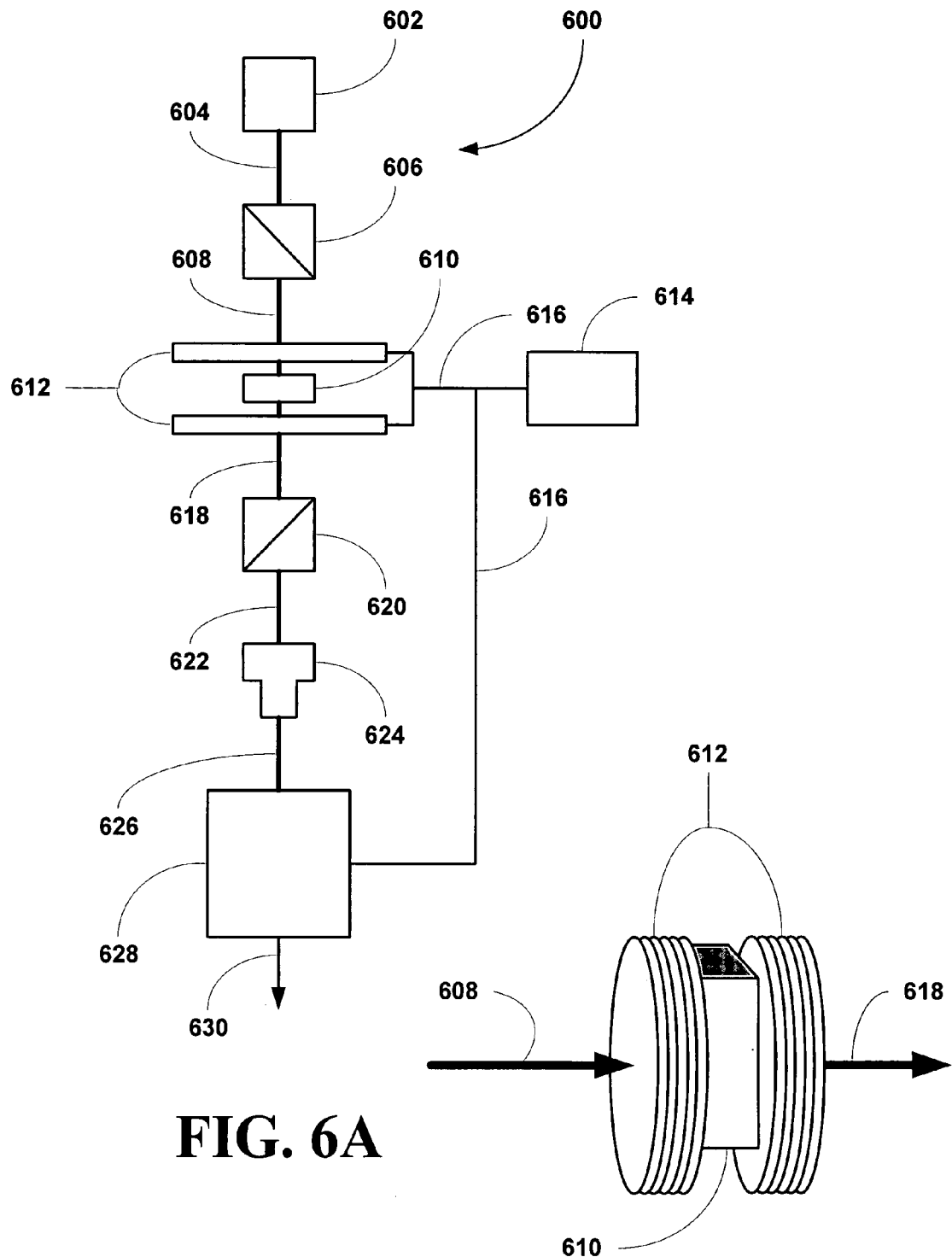
FIG. 6A depicts a block diagram of a preferred embodiment of a MOPED apparatus of this invention.
FIG. 6B depicts a block diagram of an expanded preferred Helmholtz coil and sample cell arrangement of the MOPED apparatus of FIG. 6A.

Referring now to FIGS. 6A&B a preferred embodiment of an apparatus, generally 600 is shown to include a source of bright uniform light (preferably, monochromatic light) 602, which produces an input light beam 604. The input light beam 604 is then directed into a first polarizer 606, which produces a polarized light beam 608. The polarized light beam 608 is then forwarded to a sample cell 610, which is situated in an Helmholtz coil 612 so that at any cross-section of the cell 610, the sample components within that cross-section experience a substantially uniform magnetic field, even though the magnetic field is time varying. The Helmholtz coil 612 is driven by a power supply 614, which generates an oscillatory input power signal 616 resulting in the creation of an oscillatory magnetic field across the sample cell, where any cross-section of the cell experiences a time varying, but substantially uniform magnetic field. As the light beam 608 passes through the sample, the light beam is influenced by chiral components in a sample in the sample cell 610, which is undergoing an oscillation due to the externally applied, oscillating magnetic field to produce an output light beam 618. The output light beam 618 is then directed to a second polarizer, an analyzer, 620, which is substantially crossed relative first polarizer to produce a detector light beam 622 having a small amount of polarized light from the polarized beam 608. The detector light beam 622 is then directed to a detector 624, which converts the detector light beam 622 into a detector output signal 626. The output signal 626 is then directed to a lock-in amplifier 628, which amplifies the signal 626 relative to the input power signal 616 produced by the power supply 614 (the lock-in signal) to produce a result 630 having an amplitude and phase.

In the MOPED apparatus 600 of FIG. 6A, the magnetic field applied across the sample is an oscillating magnetic field of known period and is preferably a sinusoidally varying magnetic field. The polarizers 606 and 620 are slightly uncrossed to allow some input light of the beam 608 to propagate into the detector 624 and add coherently with the polarization-rotated component of the beam 618. The lock-in detector 628 can be set to detect at various frequencies, but preferably, the lock-in is set to the second harmonic of the frequency of input power signal 616 driving the Helmholtz coil 612 to produce the magnetic-field sinusoid. In this manner, the second-order Faraday effect, which yields the chirality with high sensitivity, can be measured with all the advantages of lock-in detection and heterodyne detection. Although not shown, the apparatus 600 can also include a quarter-wave plate inserted or a photo-elastic modulator into the beam 608 after the first polarizer 606 to yield data analogous to circular dichroism.

Figures 6C, 6D:
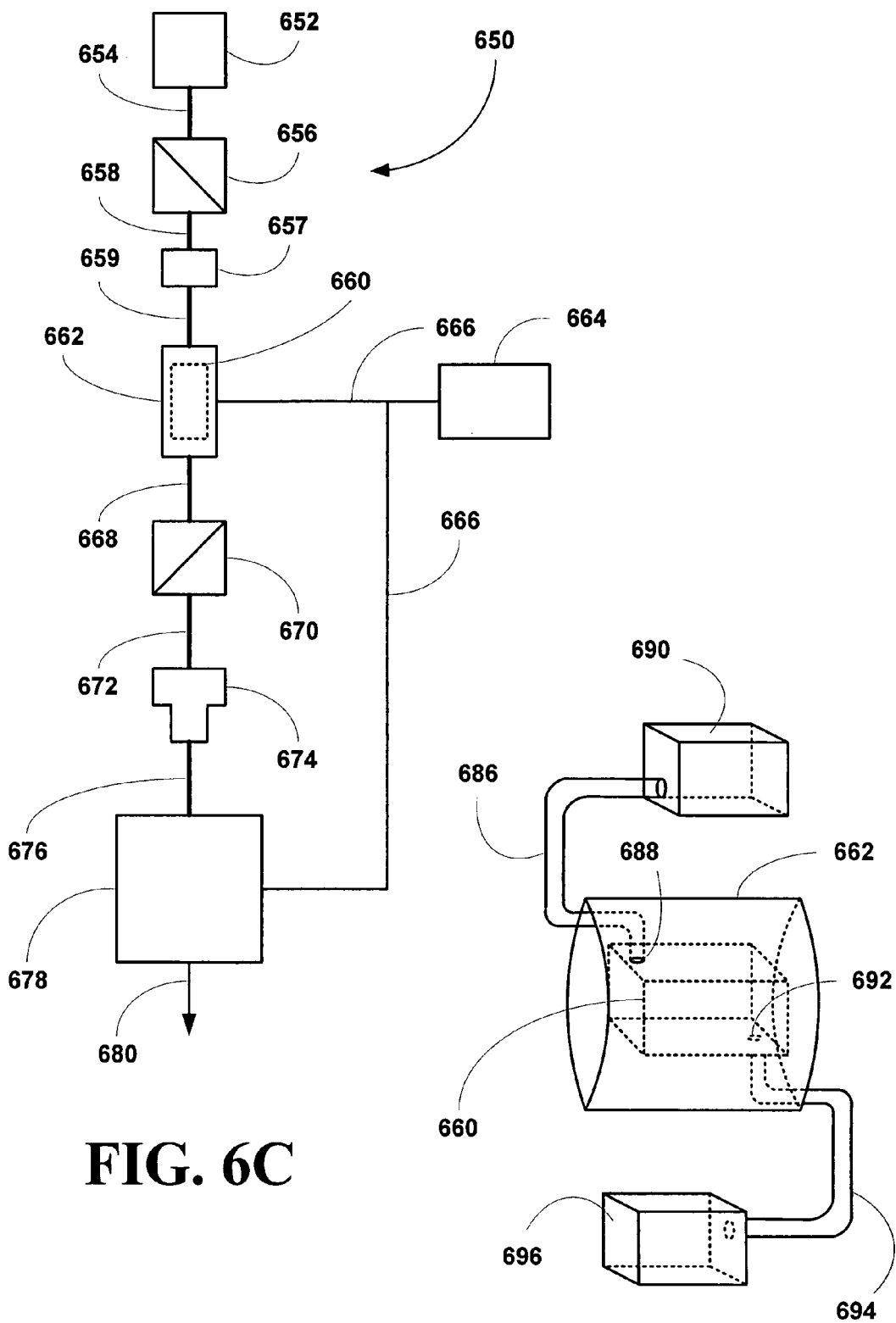
FIG. 6C depicts a block diagram of another preferred embodiment of a MOPED apparatus of this invention.
FIG. 6D depicts a block diagram of a flow cell surrounded by a solenoid within for use in either the apparatus of FIG. 6A or 6C.
Figure 9A:
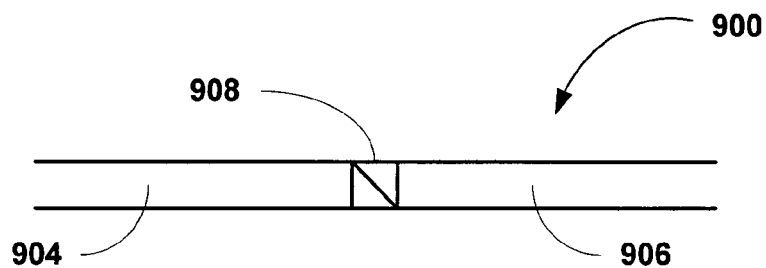
FIGS. 9A&B depict a preferred embodiment of an optical fiber/first polarizer construction and an optical fiber/second polarizer construction, respectively.
Figure 9B:
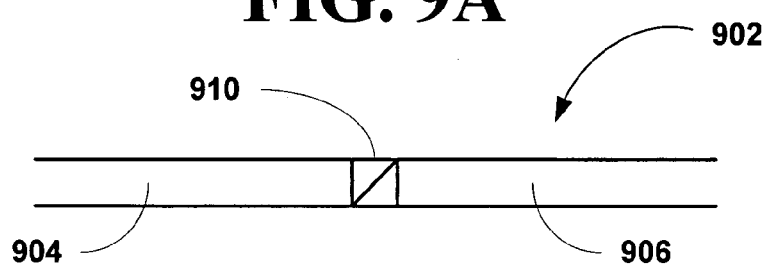
FIGS. 9C&D depict another preferred embodiment of an optical fiber/second polarizer construction and an optical fiber/second polarizer construction, respectively.
Figure 9C:
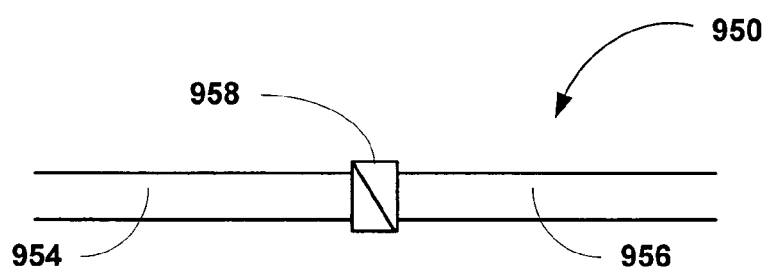
Figure 9D:
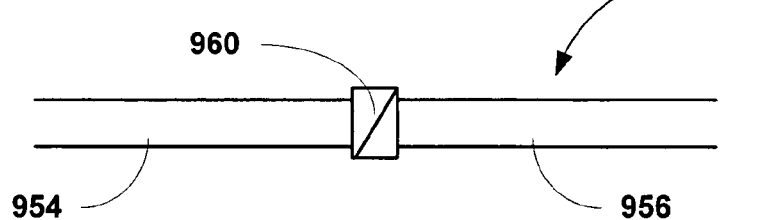

Referring now to FIGS. 6C&D, another preferred embodiment of an apparatus, generally 650 is shown to include a source of bright uniform light (preferably, monochromatic light) 652, which produces an input light beam 654. The input light beam 654 is then directed into a first polarizer 656, which produces a polarized light beam 658. The polarized light beam 658 is then forwarded to a Faraday modulator 657, which modulates the polarization of the polarized light beam 658 about a small angle to produce a modulated polarized light beam 659. The modulated polarized light beam 659 forwarded to a sample cell 660, which is situated within a solenoid 662 so that at any cross-section of the cell 660, the sample components within that cross-section experience a substantially uniform magnetic field, even though the magnetic field is time varying. The solenoid 662 is driven by a power supply 664, which generates an oscillating input power signal 666 resulting in the creation of an oscillatory magnetic field across the sample cell, where any cross-section of the cell experiences a time varying, but substantially uniform magnetic field. As the light beam 659 passes through the sample, the light beam is influenced by chiral components in a sample in the sample cell 660, which is undergoing an oscillation due to the externally applied, oscillating magnetic field to produce an output light beam 668. Although the apparatus of FIG. 6C is shown to includes a Faraday modulator 657, the apparatuses of FIGS. 6A and 8A can also includes a Faraday modulator.

The output light beam 668 is then directed to a second polarizer, an analyzer, 670, which is substantially crossed relative first polarizer to produce a detector light beam 672 having a small amount of polarized light from the modulated, polarized beam 659. The detector light beam 672 is then directed to a detector 674, which converts the detector light beam 622 into a detector output signal 676. The output signal 676 is then directed to a lock-in amplifier 678, which amplifies the signal 676 relative to the input power signal 666 produced by the power supply 664 (the lock-in signal) to produce a result 680 having an amplitude and phase.

In the MOPED apparatus 650 of FIG. 6C as with the apparatus 600 for FIG. 6A, the magnetic field applied across the sample is an oscillating magnetic field of known period and is preferably a sinusoidally varying magnetic field. The polarizers 656 and 670 are slightly uncrossed to allow some input light of the beam 659 to propagate into the detector 674 and add coherently with the polarization-rotated component of the beam 668. The lock-in detector 678 can be set to detect at various frequencies, but preferably, the lock-in is set to the second harmonic of the frequency of input power signal 666 driving the Helmholtz coil 662 to produce the magnetic-field sinusoid. In this manner, the second-order Faraday effect, which yields the chirality with high sensitivity, can be measured with all the advantages of lock-in detection and heterodyne detection. Although not shown, the apparatus 650 can also include a quarter-wave plate inserted into the beam 659 after the first polarizer 656 to yield data analogous to circular dichroism.

The cell 660 can also be a flow cell 682 as shown in FIG. 6D includes a cell body 684 situated within the solenoid 662 with a influent flow line 686 affixed to an inlet 688 and attached to a sample supply system 690. The cell body 684 also includes an outlet 692 with an effluent flow line 694 attached to a sample collection systems 696. The sample supply system 690 can be ana analytical separation apparatus such as an LC, an MPLC, an HPLC, an electrophoresis instrument, a capillary electrophoresis instrument, a GC, or any other analytical instrument designed to separate a sample into its components or a sampling apparatus which continuously or periodically samples a production stream and forwards all or a portion of the sample to the apparatus of this invention for analysis.

The use of lock-in detection, also known as lock-in amplification and phase-sensitive detection, reduces noise and improves sensitivity, taking advantage of the fact that noise exists at all frequencies and other detectors detect all frequencies and hence see all the noise. But detecting over only a small range of frequencies can reduce noise dramatically. Lock-in detection involves periodically (usually sinusoidally) modulating some aspect of the apparatus, leading to a sinusoidal modulation to the signal. The lock-in detector then multiplies the signal by a sine wave of the same frequency (its "reference wave"), and then it integrates over a short time (but over many periods of the sine wave). If a particular signal occurs at the correct frequency, and if it is in phase with the lock-in sine wave, then it yields a large result. On the other hand, any signal (or noise) at the wrong frequency (or the wrong phase) integrates to zero because the product of the noise signals and the lock-in sine wave is as often positive as it is negative. Thus, only noise of the correct frequency (and phase) contributes—in other words, much less noise contributes to the detected signal. Hence much weaker signal levels can be detected. Typically, lock-in detection yields noise reductions of $10^6$ and yields similar improvements in sensitivity. Indeed, it is common to achieve signal sensitivities of nanovolts and femtoamps. Moreover, the lock-in detector also allows detection of the relative phase between the reference sine wave and the signal sine wave very sensitively.

The Faraday effect is the tendency of an applied magnetic field to induce optical activity in a sample medium. Applying a sinusoidal current to a magnetic field generator such as a Helmholtz coil or a solenoid or the like surrounding a sample cell, which produces a sinusoidal varying magnetic field on the sample, will induce optical activity in the medium—but sinusoidally in time—yielding a sinusoidal signal at the same frequency as that of the current. Using the applied current as the lock-in reference wave (which determines the lock-in detection frequency and phase), a signal can be lock-in detected easily. This yields the well-known (linear) Faraday effect of the sample medium, and the stronger the effect, the stronger the sinusoidal variation in the transmitted light, and the larger the signal at the lock-in detector.

While the linear Faraday effect of the sample and solvent (e.g., water) is uninteresting. Most solvents and materials have a linear Faraday effect, measured by the Verdet constant, where the induced optical activity is the product of the Verdet constant, the applied magnetic field, and the medium length[31]. Fortunately, for the methodology of this invention, is a second-order Faraday effect, where the polarization rotation is proportional to the square of the magnetic field according to the following equation, which ignores third order terms:

$$[\alpha]=a+b\cdot B+c\cdot B^2$$

where B is the magnetic field, a is the chirality, b is the Verdet constant, and c is the coefficient of the second-order Faraday effect, or the second-order Verdet constant. The constant c is equivalent to or directly proportional to a substance's chirality. Thus, the second-order Faraday effect of a cell containing water and some chiral molecules is due only to the chiral molecules. And detecting the magnetically induced optical activity that scales as the square of the magnetic field yields the chirality of the solute.

Although the second-order Faraday effect (and third-order Faraday effect) was (were) recently observed only at very high DC magnetic fields (>10 Tesla)[59-61]. The second-order and/or higher Faraday effects can be easily and unambiguously detected at much lower magnetic fields by using heterodyne detection and lock-in amplification as shown in the apparatus of this invention as described more fully below.

In order to detect the second-order Faraday effect, the present invention preferably uses optical heterodyne detection (OHD). OHD involves slightly uncrossing the polarizers to deliberately yield a coherent addition of the signal light with a small amount of the input light, usually called the "local oscillator." If $E_{sig}$ is the signal electric field and $E_{lo}$ is the local-oscillator electric field, then the detected intensity, $I_{det}$, is equal to the sum of the squared magnitude of these fields:

$$I_{det}(t)=|E_{lo}(t)+E_{sig}(t)|^2$$

where, by design, $|E_{lo}(t)|^2 >> |E_{sig}(t)|^2$ and $E_{lo}$ is very stable. Multiplying out this expression yields:

$$I_{det}(t)=|E_{lo}(t)|^2+|E_{sig}(t)|^2+2Re\{E_{sig}(t)\ E_{lo}^*(t)\}$$

Since $|E_{lo}(t)|^2 >> |E_{sig}(t)|^2$, $|E_{sig}(t)|^2$ is negligible compared to $|E_{lo}(t)|^2$, and $I_{det}(t)$ can be approximated by:

$$I_{det}(t) \approx |E_{lo}(t)|^2+2Re\{E_{sig}(t)E_{lo}^*(t)\}$$

This leaves only one term containing the signal field, and it is the cross term, which is much larger than $|E_{sig}(t)|^2$, the usual signal term. Thus, OHD amplifies the signal. As a result, OHD also improves the signal-to-noise ratio significantly, and OHD yields a signal field that depends linearly on the signal field and hence the signal field and so is even more sensitive than detectors that rely on the square of the small signal.

The combination of OHD and lock-in detection is particularly powerful, where the signal beam is chopped and not the local oscillator, resulting in the cross term being the only term that is detected. This results from the fact that the $|E_{lo}(t)|^2$ term is constant and hence yields no signal at the chopping frequency. Thus, the combination of OHD and lock-in detection yields amplification and increased sensitivity simultaneously and is responsible the superior performance of the apparatuses and methods of this invention by applying a sinusoidal magnetic field across the sample, which does not affect the local oscillator. Under these conditions, the signal field becomes proportional to the optical rotation, [α]:

$$E_{sig} \propto [a+b\cdot B+c\cdot B^2]E_{input}$$

and the detected intensity $I_{det}(t)$ is given by the following equation:

$$I_{det}(t) \propto 2Re\{[a+b\cdot B+c\cdot B^2]E_{input}\ E_{lo}^*\}$$

Since the only term in the above expression that varies as the second harmonic (i.e., varies as $B^2$) is the second-order Faraday effect ($c\cdot B^2$), the signal is easily detected by lock-in detecting at the second harmonic of the applied magnetic field. Note that the presence of unwanted birefringence in the sample cell does not contribute an oscillatory component to the signal intensity and so is essentially irrelevant in these measurements. This is very convenient.

In addition, OHD provides another useful benefit. It yields the signal light wave electric field, rather than its intensity (i.e., the magnitude squared of the electric field). This means that OHD can distinguish between "in-phase" and "quadrature-phase" (90° out of phase) signals. Simply uncrossing the polarizers yields local oscillator with the same lightwave phase (not to be confused with the lock-in reference wave phase) and yields the in-phase component of the signal light wave. Alternatively, placing a quarter-wave plate in the beam introduces the quadrature phase local oscillator, which allows detection of the quadrature-phase component of the signal light wave, indicative of circular dichroism. Note that quarter-wave plates are of high optical quality and can be inserted into the beam path without reducing the sensitivity.

Thus, in addition to increased sensitivity, OHD adds an additional measured parameter to the MOPED apparatus of this invention useful results—the relative phase of the signal light with respect to the input light. This additional parameter can be used toe determine the proximity in chromophore resonances.

Finally, although the apparatus of FIG. 6A is a single channel instrument, array instruments can also be constructed either using an arrayed multichannel instrument with an array of lock-in amplifiers or the instrument can be constructed using a lock-in CCD camera under development at this time[54]. Every pixel of the lock-in CCD camera is a lock-in detector. The use of lock-in CCD cameras or an array of standard lock-in amplifiers will greatly enhance throughput of MOPED, allowing parallel measurement of hundreds or even thousands of samples, simultaneously.

Interestingly, the apparatus of this invention not only sensitively yields the magnitude of the sample chirality, but also its sign. This can be understood by the following argument. The sample (solute) optical activity adds or subtracts, depending on the relative signs of polarization rotation and the polarizer leakage.

Signal waveforms that result in the operation of the MOPED system under different modes of operation are shown in FIGS. 7A-D. In all four figures, the large amplitude sinusoid wave is the magnetic field vs. time, and the smaller curve is the output light intensity (in the absence of any polarizer leakage). Looking at FIG. 7A, a constant output signal results in the absence of the Faraday effect, even if chirality is present. Looking at FIG. 7B, in the absence of chirality, the linear Faraday effect induces sinusoidal output light. Looking at FIG. 7C, the presence of both chirality and the Faraday effect yields a phase-shifted signal intensity. And looking at FIG. 7D, the presence of higher-order Faraday effects introduces distortions in the intensity vs. time curve. In this case, detection at higher lock-in frequencies yields the higher-order terms. The second-order Faraday term is a manifestation of the chirality and can be more sensitively detected than the simple chirality, which doesn't lend itself to lock-in detection. The third mode involves using the phase shift of the lock-in detected signal, which yields, not the Faraday effect due to the solute, but the actual chirality (and also its sign). When some chiral solute is present, independent of the applied magnetic field, it will yield a phase shift in the signal wave compared to that of the reference wave as shown in FIG. 7C.

For example, if the magnetic-field-induced optical activity is of opposite sign to that of the solvent optical activity, then some magnetic field will be required to cancel out the solute chirality. If the opposite is true, then some magnetic of the opposite sign is required to cancel out the solute chirality. Thus the phase shift between the signal and reference waves (which is measured sensitively by the lock-in) yields the solute chirality relative to the water linear Faraday effect. And since water's linear Verdet constant is well known, it is easy to extract out the solute chirality, including its sign.

The MOPED apparatus and method also provide greater generality. While, traditional polarimetry provides only one parameter for a given medium: its chirality, the present invention is capable of determining the chirality and other parameters to aid in the characterization of a medium giving the present apparatus and method greater predictive power. Additional parameters or measured characteristics can be achieved using the present apparatus in a simple manner by detecting a sample at several harmonics depending on the sensitivity of the MOPED instrument. Thus, the MOPED apparatus and method is capable of yielding, not only the chirality, but also various higher-order Faraday-effects. These additional data, parameters, or characteristics of the sample are available because the apparatus of this invention can be locked-in higher harmonics of the frequency of the applied magnetic field, yielding higher-order terms of the Fourier series expansion of the induced optical activity vs. magnetic field. These the higher-order terms are particularly useful for measuring mixtures with several species contributing to overall optical rotation.

Referring now to FIGS. 8A-E, another preferred apparatus of this invention, generally 800 is shown to include a source of monochromatic light 802. The light from the light source 802 is directed into a first bundle of optical fibers 804 as shown in FIG. 8B, each fiber 805 carrying a light beam. The first optical fiber bundle 804 terminates at a first polarizer 806, which polarizes each light beam from each optical fiber 805 in the bundle 804. The resulting polarized light beams are directed into a second bundle of optical fibers 808, which forwards the beam to a sample cell 810 including a corresponding sample chamber 811 for each optical fiber 809 in the bundle 808. The multi-chambers cell 810 is situated in an Helmholtz coil 812 so that at any cross-section all of the chambers 811 in the cell 810 the components of the sample within that cross-section experience a substantially uniform magnetic field, even though the magnetic field is time varying experience a substantially uniform magnetic field. The Helmholtz coil 812 is driven by a power supply 814, which generates an oscillatory input power signal 816 resulting in the creation of an oscillatory magnetic field across the sample cell, where any cross-section of the cell experiences a time varying, but substantially uniform magnetic field. As each polarized light beam delivered by the bundle 808 passes through its corresponding sample, the polarized light beam is influenced by chiral components in the corresponding sample, while the sample components are undergoing an oscillation due to the externally applied, oscillating magnetic field to produce output light beams which are directed into a third bundle of optical fibers 818. The output light beams carried on a corresponding optical fiber 819 in the bundle 818 are then directed to a second polarizer, an analyzer, 820, which is substantially crossed relative first polarizer to produce detector light beams carried on a fourth bundle of optical fibers 822 of fibers 823. Because the polarizers 806 and 820 are slightly misaligned from being out-of-phase, the detector light beam will include a small amount of polarized light from the polarized beam carried by the bundle 808. The detector light beams carried by the bundle 822 are then directed to a detector 824, which converts each detector light beam into detector output signals carried on a wire bundle 826. The output signals carried in the bundle 826 are then directed to a lock-in amplifier 828, which amplifies each signal relative to the input power signal 816 produced by the power supply 814 (the lock-in signal or a harmonic thereof) to produce a result of each ample 830 having an amplitude and phase. Looking at FIG. 8C, a preferred embodiment of a multi-chambered cell 840 is shown to be substantially rectangular cell 810 with cylindrical chambers 811. It should be apparent from FIGS. 8B and C that some type of an interface is required to conform the bundle format of the optical fiber bundle to its corresponding chamber format. Such an interface or manifold 850 is shown in FIG. 8D, where the manifold 850 includes a rectangular body 852 which conforms to the ends 842 of the cell 840 and includes optical fiber holders 854 which center the optical fibers relative to an opening 844 of each chamber 811. Looking at FIG. 8E an alternate cell 860 is shown to includes a diamond shaped body 810 and cylindrical chambers 811. Of course, the sample of the cell can be of any shape including, without limitation, circular, oval, square, rectangular, triangular, pentagular, etc.

Referring now to FIGS. 9A-D, two preferred embodiments of optical fiber-polarizer construction are shown. Looking at FIGS. 9A&B, an optical fiber-first polarizer construct, generally 900, and its corresponding optical fiber-second polarizer construct, generally 902. The constructs 900 and 902 include a first optical fiber 904 and a second optical fiber 906 and polarizers 908 or 910 situated therebetween, where the polarizers 908 and 910 are substantially the same size as the optical fibers 904 and 906, and are oriented in a cross or substantially crossed configuration. Looking at FIGS. 9C&D, an optical fiber-first polarizer construct, generally 950, and its corresponding optical fiber-second polarizer construct, generally 952. The constructs 950 and 952 include a first optical fiber 954 and a second optical fiber 956 and polarizers 958 or 960 situated therebetween, where the polarizers 958 and 690 are larger than the same size as the optical fibers 954 and 956, and are oriented in a cross or substantially crossed configuration.

Referring now to FIGS. 10A-D, two alternate preferred embodiments of optical fiber-polarizer construction are shown. Looking at FIGS. 10A&B, an optical fiber-first polarizer construct, generally 1000, and its corresponding optical fiber-second polarizer construct, generally 1002. The constructs 1000 and 1002 include a first plurality of optical fibers 1004 and a second plurality of optical fibers 1006 and polarizers 1008 and 1009 situated therebetween, where the polarizers 1008 and 1009 are sufficiently sized to accommodate all of the fibers 1004 and 1006, and are oriented in a cross or substantially crossed configuration. Looking at FIGS. 10C&D, the constructs 1000 and 1002 are shown looking at faces 1010 and 1011 where individual fibers 1012 contact the polarizers 1008 and 1009 surfaces 1014 and 1015, respectively.

Some practical issues associated with the apparatuses and methods of this invention related to the value of the applied magnetic field that is required induce an oscillatory response to the analyte in the sample. The applied field is generally of a relatively low strength, which can be easily generated by standard power supplies and magnetic field generators such as Helmholtz coils and solenoids and torodial coils. Because lock-in and optical heterodyne detections are so sensitive, it is not necessary to achieve large values of induced optical activity, which require high magnetic field strength, generally several Tesla. Commercially available Helmholtz coils and solenoids are capable of producing magnetic field of a few Gauss, with higher field strengths preferred, from an amp of current are suffice and are of sufficient size to cover an entire 96-well plate allowing the plate to be inserted into the Helmholtz coil and polarized light to be directed into each well individually or as described in FIG. 8A. Suppliers of Helmholtz coils include Magnetic Instrumentation Inc. or Lake Shore Cryotronics using power supplies such as those available from Kentronix to drive the field modulation are easily found. For the purposes of this invention a Helmholtz coils comprises two coaxial circular current loops with the same radius, separated from each other by one radius. In other words, the loops are separated by a distance 1, where I is the radius of the coils. That is, a Helmholtz coil arrangement is two circular coils separated by a distance equal to the coil radius. A solenoid is a simple electromagnetic comprising a single coil which generates a substantially uniform field in the interior of the coil when current is passed through the coil. A torodial coil is an electromagnetic comprising of a coil in a doughnut or torus shaped winding.

Finally, it should be pointed out that sinusoidally modulating the magnetic field applied to a polarimetry sample is practically an ideal application of lock-in and heterodyne detection and hence is very easy to do, as shove in FIGS. 6A-D. These techniques add no components in the beam path, respecting the integrity of the high-quality Calcite polarizers, and adding greatly to the achieved sensitivity, while allowing record-high throughput. In addition, due to the impressive sensitivity of lock-in detection, detecting the linear and nonlinear Faraday effect is likely always to be much more sensitive than DC-detecting the optical activity as is usually done. Owing to increased sensitivity, smaller sample sizes and/or lower concentrations can be analyzed, vastly expanding the potential applications of polarimetry.

In systems of this invention that involve light source modulation [$\theta(t)=\cos(\phi t)$] and sample cells having a plurality of sample chambers, the light delivery system can comprise a fiber optic bundle, one optical fiber per chamber for irradiation, while the transmitted light is transferred to the analyzer via a second fiber optic bundle, one optical fiber per chamber. The resulting analyzed light is then ported to the detector via a third fiber optic bundle, one optical fiber per chamber for detection. The array of detected signals is then passed onto a parallel lock-in amplifier or a lock-in CCD for analysis. Although normal optical fibers can be used, it is preferred to use optical fibers that do not adversely affect polarization, i.e., the optical fibers maintain substantially the same polarization of the input light as the output light. It is preferred, of course, that no alteration occur. However, in the real world, the difference between initial polarization and final polarization should be less than about 1 part in 10,000, preferably, 1 part in 100,000 and particularly 1 part in 1,000,000.

One preferred the fiber optic light delivery system includes a first bundle of fibers, one fiber for each chamber, where each fiber includes an initial length of fiber and a second length of fiber with a first polarizer interposed therebetween, where the proximal end of the first length receives incident light from a substantially monochromatic light source and the distal end of the second length emits light having a first polarization, where the delivery system can also includes a polarization modulator situated after the polarizer. This first bundle is then arrayed to irradiate a sample in each sample chamber of the cell. The delivery system also includes a second fiber optic bundle, one fiber for each chamber, where each fiber includes a first length of fiber and a second length of fiber with a second polarizer interposed therebetween, where the proximal end of the first length receives light passing through the chambers and the distal end of the second length emits light passing through the second polarizer into an array detector, one detector element for each analyzed light stream or into a detector capable of detecting all of the light from each fiber independently. A particular preferred fiber optical delivery system includes polarizers that are substantially the same size or slight larger than the fiber itself.

Possible Pitfalls and Alternative Approaches

While detecting nonlinear Faraday effects is essentially immune to linear Faraday effects, one concern in the development in any piece of analytical equipment is the sources of noise that reduce sensitivity and interfere with analysis. One benefit of the lock-in detector is noise isolation, but there are several potential effects that can interfere. The magnetic coil may induce electromagnetic interference ("pick-up") in the lock-in at its frequency, fortunately not at the harmonics. However, such effects can be reduced or eliminated by good shielding of the amplifier from the magnetic field as is well-known in the art. One alternate approach to obtain extremely accurate measurements at the magnetic field frequency, is to independently modulate the laser beam and use a separate lock-in amplifier locked to the sum of the frequencies of the magnetic field and the laser modulations. Using these two lock-in amplified signals, each with independent sources of noise, allows for noise reductions in the combined signal.

Another source of noise is the birefringence of the material in the walls of the liquid container. However, birefringence is not modulated by the magnetic field, and so is not detected. If a magnetically induced birefringence is present, OHD is designed to separate out this effect by detecting only the in-phase component. Zeroing the polarizers to null this DC contribution of the container before any measurement minimizes this effect. The best strategy to avoid birefringence from stress in materials will be to reflect the analyzing beam off the sample bottom rather than passing it through a transparent window: first by directing the light beam at the bottom of the sample avoids any stress in the material entirely and secondly, the path length doubles by passing the beam through the sample twice, thus increasing the raw signal.

Lock-in detection is relatively immune to solvent and any other dc effects. Solvent effects can play an important role in alternative versions of the MOPED apparatus operating under condition that result in the measurement of only the linear Verdet effect. While the linear Verdet constant of water as the most likely solvent is quite small, the relative concentration is large (55.6 M for pure water). However, the present invention is designed to use lock-in detection, analyzed at the second-order Faraday effect, and especially operation at harmonics of the magnetic field frequency inherently avoid all of these DC and first-order effects, which are the bane of standard polarimetry.

Additional solvent effects such as adsorption, scattering from particulate, and local heating from the laser can be minimized, if a problem, by remedies such as using a laser wavelength in non-absorbing regions of the spectrum, filtering the sample, and/or using a low intensity (but high power) laser. Contributions from chiral biological samples to signal background can be avoided or reduced by a blank sample of these components so that the spectra can be subtracted or the blank signal can be used in a feed back loop in an out-of-phase format to cancel or reduce the background. As none of these effects yields a sinusoidally modulated contribution, the lock-in would ignore them.

Light-mediated racemization or degradation of analytes can be another effect of concern, but should be no more problematic than in current polarimeters. Mandelic acid is known to be light-sensitive as are many therapeutic agents[12]. Picking an appropriate analysis wavelength or, with unknown analytes, minimization of light intensity in the analysis beam will reduce such error. The trade-off between using a low intensity wide beam (diameter d of about 1 mm) to minimize these effects compared to a tight beam (diameter d of about 0.1 mm) of same intensity to minimize contribution from window birefringence is unknown.

One feature of the present invention is the use of a magnetic field generator and a power supply capable to supply periodically varying power (current and/or voltage) to the magnetic generator to place the sample under the influence of a periodically varying magnetic field. Although any magnetic field generator capable of generating periodically varying magnetic field can be used, the preferred generators are Helmholtz coils, solenoids and toroidal coils. Although standard Helmholtz coils can be used, new Helmholtz coils can be used as well such as though disclosed in described in the following references: "An improved Helmholtz coil and analysis of its magnetic field homogeneity," J. Wang, S. She and S. Zhang, Review of Scientific Instruments, 73, 2175-2179 (2002); "Magnetic Field Calibration: Unwinding The Helmholtz Coil," I. Straus, Curtis-Straus LLC Littleton, Mass., Conformity, 40-44 (May 2002), incorporated herein by reference. The present invention disclosed in FIGS. 6C&D using a solenoid is designed to also be useful in the case of HPLC flow through detector instruments where one does not need to remove the sample chamber to introduce the sample. One feature of the the instruments of this invention using a Helmholtz coil is that the instrument has an open format and a very uniform magnetic field between the two coils. However, some non-uniformity could be normalized out if the departure from ideality was known, simulated, or measured. Preferably, of course, the magnetic field is substantially homogeneous or uniform at any cross-section of the sample cell at any given time and any inhomogeneity should be less than or equal to about 5%, preferably, less than or equal to about 2% and particularly, less than or equal to about 1%.

The modulation of the polarized light beam exiting the first polarizer can be accomplished both mechanically and electrooptically. Mechanically, the beam is dithered about the polarization angle to produce a small angle modulation about that angle using a ½ wave plate. However, the preferred modulation is accomplished electro-optically using a Faraday modulator, which comprises a Faraday rotator and optionally a low bandpass filter (precision synchronous) as described in "Precision synchronous polarimeter with linear response fro the measurement of small rotation angles," A. Arnaud, F. Silveira, E. M. Frins, A. Dubra, C. D. Percianite, and J. A. Ferrari, Applied Optics, 39, 2601-2604 (2000).

Suitable light sources for use in the present invention include, without limitation, high intensity, monochromatic polarized laser light sources such as photo-emitting diodes, gas lasers such as He—Ne lasers, solid state laser or the like. Preferred light sources are high intensity, monochromatic polarized laser light sources. The apparatus of this invention can also be operated with several lasers of different emission frequencies (wavelengths). After the multi-frequency light passes through the sample, the light is forwarded to the analyzer and then to a diffraction grating for separating the probing light into different wavelengths, which are then forwarded onto separate detectors. Alternatively, laser sources producing multiple emission lines such as ion lasers can be used in a similar manner to multi-lasers. Broad wavelength and tunable laser sources can also be used such as fiber lasers. These broadband light sources are especially well suited for use with a CCD lock-in detector or an array of lock-in detectors to simultaneously obtain information over tunable or multiple wavelengths. In addition, high intensity broad band sources of light such as tungsten or halogen lamps can be used with optical filters prior to the first polarizer, after the analyzing polarizer, or separated into a spectrum of wavelengths by a diffraction grating. Xenon flash sources can also be used, which are capable of producing high intensity broad band light which can then be either filtered to a given bandwidth or used directly with diffraction gratings to separate wavelengths and send the separated wavelengths to a CCD lock-in detector or an array of lock-in detectors.

Suitable input light modulation include, without limitation, a Faraday modulator, the preferred method due to its ability to electro-optically modulate the signal with any chosen wave form, a rotating, oscillating or dithering ½ wave plate apparatus, a kerr cell, a pockels cell or the like. These modulators a designed to be inserted between the light source and the first polarizer. The rotating, oscillating or dithering wave plate modulates the state of linear polarization of the beam about the null, thus time varying the leakage as accomplished in the case of the Faraday modulator. Dithering is preferable to rotating, because the large leakage of light introduced when passing through maximum transmission may create detector saturation problem. A kerr cell modulates an electric field perpendicular to the input polarized light causing the cell to function as a variable waveplate with frequency responses of up to 10E10 Hz. A pockels cell operates with a transverse or longitudinal format and is a linear electro-optical effect, where the applied voltage induces a birefringence in the material between the plates when the voltage is applied. These pockel cell modulators can modulate light up to about $25 \times 10^9$ Hz.

Suitable polarizers for use in this invention include, without limitatin, naturally occurring calcite polarizers, which is preferred and have the highest extinction ratios ($10^{-6}$), synthetic polarizers such as alpha-BBO, a synthetic crystal known to posses high extinction coefficients over a defined wavelength ranges (400-700 nm), dichroic sheet polarizers, with extinction values of about $10^{-5}$ and are much less expensive and readily available or any other polarizer.

REFERENCE

The following references are cited with superscripted number in the above application:

1. *Chiral Separations by HPLC*. Ellis Horwood, Chichester. 1989.
2. Angelaud, R., Y. Matsumoto, T. Korenaga, K. Kudo, M. Senda, and K. Mikami. 2000. Optical rotation per refractive index unit, or enantiomeric (e) factor, for screening enantioselective catalysts through asymmetric activation or carbohydrates. Chirality 12:544-547.
3. Arnold, F. H. 1998. Design of Directed Evolution. Ace. Chem. Res. 31:125-131.
4. Arnold, F. H., P. L. Wintrode, K. Miyazaki, and A. Gershenson. 2001. How enzymes adapt: lessons from directed evolution. Trends Biochem. Sci. 26:100-106.
5. Bertucci, C., V. Andrisano, V. Cavrini, and E. Castiglioni. 2000. Reliable assay of extreme enantiomeric purity values by a new circular dichroism based HPLC detection system. Chirality 12:84-92.
6. Bhatia, P. S., J. P. Holder, and J. W. Keto. 1997. J. Opt. Soc. Amer. B 14:263.
7. Bi, X., T. S. Haque, J. Zhou, A. G. Skillman, B. Lin, C. E. Lee, I. D. Kuntz, J. A. Ellman, and G. Lynch. 2000. Novel cathepsin D inhibitors block the formation of hyperphosphorylated tau fragments in hippocampus. J. Neurochem. 74:1469-1477.
8. Bommarius, A. S., K. H. W. Drauz, M.-R. Kula, and C. Wandrey. 1994. Some new developments in reductive amination with cofactor regeneration. Biocatalysis 10:37-47.
9. Bommarius, A. S., M. Schwarm, and K. Drauz. 1998. Biocatalysis to Amino Acid-based Chiral Pharmaceuticals—Examples and Perspectives. J. Mol. Cat. B: Enzymatic 5:1-11.
10. Bylina, E. J., W. J. Coleman, M. R. Dilworth, S. J. Robles, M. A. Tanner, M. M. Yang, and D. C. Youvan. 2000. Solid-Phase Enzyme Screening. ASM News211-217.
11. Chankvetadze, B. 1997. Capillary Electrophoresis in Chiral Analyis. Wiley, Chichester.
12. Crossley, R. 1995. Chirality and the Biological Activity of Drugs. CRC Press, Boca Raton.
13. d'Angelo, J., J. F. Mouscadet, D. Desmaele, F. Zouhiri, and H. Leh. 2001. HIV-1 integrase: the next target for AIDS therapy? Pathol. Biol. (Paris) 49:237-246.
14. Dbaibo, G. S. 2000. Old and new targets of antibacterial therapy. J. Med. Liban. 48:177-181.
15. Delagrave, S., D. J. Murphy, J. L. Pruss, A. M. Maffia, III, B. L. Marrs, E. J. Bylina, W. J. Coleman, C. L. Grek, M. R. Dilworth, M. M. Yang, and D. C. Youvan. 2001. Application of a very high-throughput digital imaging screen to evolve the enzyme galactose oxidase. Protein Eng 14:261-267.
16. Diaz, N., G. Sanchez, A. Gallardo, and G. Pareja. 2001. HPLC enantiomeric resolution of (+)-cinchonine and (−)-cinchonidine with diode-laser polarimetric detection. Instrumentation Science & Technology 24:47-56.
17. Dickson, B. J. 2000. Chirality, magnetism and light. Nature 405:895-896.
18. Driscoll, A. L. and W. Vaughan. 1978. Handbook of Optics. McGraw-Hill, N.Y.
19. Du, X., E. Hansell, J. C. Engel, C. R. Caffrey, F. E. Cohen, and J. H. McKerrow. 2000. Aryl ureas represent a new class of anti-trypanosomal agents. Chem. Biol. 7:733-742.
20. Eesly, G. L. 1981. Coherent Raman Spectroscopy. Pergamon, Oxford.
21. Fox, S. J., M. A. Yund, and S. F. Jones. 2000. Assay innovations vital to improving HTS. Drug Discoverer & Development40-43.
22. Francis, M. B., T. F. Jamison, and E. N. Jacobsen. 1998. Combinatorial libraries of transition-metal complexes, catalysts and materials. Curr. Opin. Chem. Biol. 2:422-428.
23. Gauglitz, G. 2000. Optical detection methods for combinatorial libraries. Curr. Opin. Chem. Biol. 4:351-355.
24. Gibbs, P. R. *Studies in Biocatalysis,* 2000. University of Houston. Ref Type: Thesis/Dissertation
25. Gibbs, P. R. Willson, R. C., Uehara, C. S., and Nguyen, P. T. Imaging Polarimetry for Chiral Screening of Combinatorial Libraries. 01003/01PRV. 2001. Patent
26. Gillham, E. J. 1957. A High-precision Photoelectric Polarimeter. Journal of Scientific Instruments 435-439.
27. Gillham, E. J. [U.S. Pat. No. 3,155,762]. Nov. 1, 1964. Patent
28. Groger, H. 2001. Enzymatic Routes to Enantiomerically Pure Aromatic a-Hydroxy Caboxylic Acids:A Further Example for the Diversity of BioCatalysis. Adv. Synth. Catal. 343:547-558.
29. Hartley, B. S., N. Hanlon, R. J. Jackson, and M. Rangarajan. 2000. Glucose isomerase: insights into protein engineering for increased thermostability. Biochim. Biophys. Acta 1543:294-335.
30. Hawk, P. B. 1913. Pratical Physiological chemistry. P. Blakiston's &Co., Philadelphia.
31. Hecht, E. 1998. *Optics, Addison Wesley Longman, N.Y.*
32. Hertzberg, R. P. and A. J. Pope. 2000. High-throughput screening: new technology for the 21st century. Curr. Opin. Chem. Biol. 4:445-451.
33. Hidalgo, M. and S. G. Eckhart. 2001. Development of Matrix Metalloproteinase Inhibitors in Cancer Therapy. Journal of the National Cancer Institute 93:178-193.
34. Jandeleit, B., D. J. Schaefer, T. S. Powers, R. W. Turner, and W. H. Weinberg. 1999. Combinatorial materials science and catalysis. Angew. Chem. Int. Ed. 38:4000-4038.
35. Karno, N. G., T. J. Edkins, and D. R. Bobbitt. 2001. Direct Specific Rotation Measurements of Amino Acids, Dipeptides, and Tripeptides by Laser-Based Polarimetry. Chirality 11:187-194.
36. Kelvin, L. 1904. *Baltimore lectures*. Clay, London.
37. Konig, W. A. 1992. Gas Chromatographic Enantiomer Separation with Modified Cylcodextrins. Huthig, Heidelberg.
38. Krix, G., A. S. Bommarius, K. Drauz, M. Kottenhahn, M. Schwarm, and M.-R. Kula. 1997. Enzymatic reduction of -keto acids leading to L-amino acids or D-hydroxy Acids. Biotechnology 53:29-39.
39. Levenson, M. D. and J. J. Song. 2001. Coherent Raman Spectroscopy, p.293-373. In M. S. Feld and V. S. Letoklov (eds.), Coherent Nonlinear Optics. Springer-Verlag, Berlin.
40. Luond, R. M., J. H. McKie, K. T. Douglas, M. J. Dascombe, and J. Vale. 1998. Inhibitors of glutathione reductase as potential antimalarial drugs. Kinetic cooperativity and effect of dimethyl sulphoxide on inhibition kinetics. J. Enzyme Inhib. 13:327-345.

41. May, O., P. T. Nguven, and F. H. Arnold. 2000. Inverting enantioselectivity by directed evolution of hydantoinase for improved production of L-methionine. Nat. Biotechnol. 18:317-320.
42. Michels, P. C., Y. L. Khmelnitsky, J. S. Dordick, and D. S. Clark. 1998. Combinatorial biocatalysis: a natural approach to drug discovery. Trends Biotechnol. 16:210-215.
43. Pasteur, L. 1848. R. Acad. Sci 26:535-538.
44. Patel, R. N. 2000. *Stereoselective Biocatalysis*, Marcel Dekker, New York, N.Y.
45. Pfeiffer, C. C. 1956. Science 124:29-31.
46. Reetz, M. T. 2001. Combinatorial and Evolution-Based Methods in the Creation of Enantioselective Catalysts. Angew. Chem. Int. Ed. 40:284-310.
47. Reetz, M. T., K. M. Kuhling, H. Hinrichs, and A. Deege. 2000. Circular dichroism as a detection method in the screening of enantioselective catalysts. Chirality 12:479-482.
48. Ren, S. and E. J. Lien. 2001. Development of HIV protease inhibitors: a survey. Prog. Drug Res. Spec No: 1-34.
49. Rosenblum, L. L., G. Patton, A. R. Grigg, A. J. Frater, D. Cain, O. Erlwein, C. L. Hill, J. R. Clarke, and M. O. McClure. 2001. Differential susceptibility of retroviruses to nucleoside analogues. Antivir. Chem. Chemother. 1.2: 91-97.
50. Shaw, T., J. S. Nixon, and K. M. Bottomley. 2000. Metalloproteinase inhibitors: new opportunities for the treatment of rheumatoid arthritis and osteoarthritis. Expert. Opin. Investig. Drugs 9:1469-1478.
51. Sheldon, R. A. 1993. Chirotechnology: industrial synthesis of optically active compounds. Marcel Dekker, New York, N.Y.
52. Shurcliff, W. A. 1962. Polarized light. Harvard University Press, Cambridge. Mass.
53. Smith, H. S., P. Burke, A. Lompado, E. Tanner, and L. W. Hillman. 2000. Mueller matrix imaging polarimetry in dermatology. Proceedings of SPIE 3911.
54. Sprig, T., P. Seitz, O. Vietze, and F. Heitger. 1995. IEEE J. Quant. Electron 31.
55. Stinson, S. C. 1994. Chiral Drugs. Chem. Eng. News38-72.
56. Stinson, S. C. 1999. Chiral Drug Interactions. Chem. Eng. News101-120.
57. Stinson, S. C. 2001. Chiral Drugs. Chem. Eng. News55-78.
58. Sundberg, S. A. 2000. High-throughput and ultra-high-throughput screening: solu. Curr. Opin. Biotechnol. 11:47-53.
59. Surma, M. 1997. Magneto-optical circular birefringence of a chiral medium in high magnetic field. Molecular Physics 90:993-997.
60. Surma, M. 1998. Experimental evidence of the B2 and B3 dependent circular birefringence of chiral molecules in high magnetic fields. Molecular Physics 93:271-278.
61. Surma, M. 1999. Correlation between quadratic magnetic field induced circular birefringence and the natural optical acitivity of chiral media. Molecular Physics 96:429-433.
62. Trebino, R. 2002. *Frequency Resolved Optical Gating: The Measurement of Ultrashort Laser Pulses.* Kluwer Academic Publishers, Boston.
63. Turner, G. L. 1983. *Nineteenth Century Scientific Instruments*. Sotheby/U Cal., London/Berkeley.
64. Wahler, D. and J. L. Reymond. 2001. Novel methods for biocatalyst screening. Curr. Opin. Chem. Biol. 5:152-158.
65. Willems, L., G. R. van der, and K. de Beule. 2001. Itraconazole oral solution and intravenous formulations: a review of pharmacokinetics and pharmacodynamics. J. Clin. Pharm. Ther. 26:159-169.
66. Willson, R. C., D. R. Hill, and P. R. Gibbs. 2001. High-Throughput Screening of Catalyst Libraries In 1. Sucholeiki (ed.), Marcel Dekker, N.Y.
67. Wozniak, S. 1998. Optically induced circular and axial birefringence and dichroism in chiral liquids. Molecular Physics 94:789-802.
68. Zaks, A. 2001. Industrial biocatalysis. Curr. Opin. Chem. Biol. 5:130-136.
69. Zawodny, R., S. Wozniak, and G. Wagniere. 1997. On quadratic dc magnetic field-induced circular birefringence and dichroism in isotropic chiral media. Molecular Physics 91:165-172.
70. Zucker, S., J. Cao, and W. T. Chen. 2000. Critical appraisal of the use of matrix metalloproteinase inhibitors in cancer treatment. Oncogene 19:6642-6650.
71. [Docket No. 97D-0448] International Conference on Harmonisation; Guidance on Q&A Specifications:Test Procedures and Acceptance Criteria for New Drug Substances and New Drug Products: Chemical Substances. Federal Register/Vol. 65, No. 251/Friday, Dec. 29, 2000/ Notices Food and Drug Administration.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for detecting optical properties of an analyte in a sample comprising the steps of:

exposing a sample including a chiral analyte to a periodically varying magnetic field across a sample;

passing an incident polarized light beam having a narrow bandwidth through the sample, while the sample is under the influence of the periodically varying magnetic field to produce an output light beam, where the narrow bandwidth comprises light having a base frequency and light having a frequencies within about 1% of the base frequency and comprising less than about 1% of the light intensity;

removing substantially all of the incident polarized light from the output beam; detecting the output beam to produce an output signal; and lock-in amplifying the output signal, where the lock-in signal is a frequency of the periodically varying magnetic field or a harmonic thereof to produce a magnitude and phase of the output signal.

2. The method of claim 1, wherein the periodically varying magnetic field is a sinusoidally varying magnetic field.

3. The method of claim 1, wherein the narrow bandwidth comprises light having a base frequency and light having a frequencies within about 0.5% of the base frequency and comprising less than about 0.5% of the light intensity.

4. The method of claim 1, wherein the narrow bandwidth comprises light having a base frequency and light having a frequencies within about 0.1% of the base frequency and comprising less than about 0.1% of the light intensity.

5. The method of claim 1, wherein the narrow bandwidth comprises a single frequency.

6. The method of claim 1; wherein the light is light from a laser.

7. A polarimeter method comprising the steps of:
exposing a sample including a chiral analyte to a periodically varying magnetic field across a sample;
passing an incident polarized light beam hasting a narrow bandwidth through the sample, while the sample is under the influence of the periodically varying magnetic field to produce an output light beam, where the narrow bandwidth comprises light having a base frequency and light having a frequencies within about 1% of the base frequency and comprising less than about 1% of the light intensity;
optically heterodyne detecting the output beam to produce an output signal; and lock-in amplifying the output signal, where the lock-in frequency is a frequency of the periodically varying magnetic field or a harmonic thereof to produce a magnitude and phase of the output signal.

8. An apparatus for enhanced detection of optical properties of analytes, where the apparatus comprises:
a light source adapted to generate an incident light beam having a narrow bandwidth; a first polarizer adapted to polarize the incident light beam to produce a polarized light beam;
a sample cell containing a sample including a chiral analyte adapted to receive the polarized beam and produce an output light beam;
a magnetic field generator surrounding the cell, and adapted to generate a periodically varying magnetic field across the cell such that the analyte is exposed to a periodically varying magnetic field as the polarized light bean passes through the cell;
a power supply adapted to supply a periodically varying electric current to the magnetic field generator to generate the periodically varying magnetic field;
a second polarizer or analyzer aligned substantially out-of-phase with the first polarizer to block substantially all of the incident polarized light to form an analyzed, output light beam;
a detector adapted to receive the analyzed output light beam and produce an output signal; and
a lock-in amplifier adapted to amplify the output signal and generates an amplitude and phase of the output signal, where the lock-in frequency is the frequency of the periodically varying magnetic field or a harmonic thereof.

9. The apparatus of claim 8, further comprising a modulator adapted to modulate the polarization of the polarized beam prior to being received by the sample cell.

10. The apparatus of claim 8, wherein the lock-in amplifiers is locked to a combined frequency comprising frequency of the power supply and the frequency of the modulator.

11. An apparatus for enhanced detection of optical properties of analytes, where the apparatus comprises:
a light source adapted to generate an incident beam of light having a narrow bandwidth;
a first polarizer adapted to polarize the incident light beam to produce a polarized light beam;
a flow cell into which a sample including a chiral analyte is supplied, where the cell is adapted to receive the polarized beam and produce an output beam;
a magnetic field generator surrounding the cell and adapted to generate a periodically varying magnetic field across the cell such that the analyte is exposed to a periodically varying magnetic field as the polarized light beam passes through the cell;
a power supply adapted to supply a periodically varying electric current to the magnetic field generator to generate the periodically varying magnetic field;
a second polarizer or analyzer aligned substantially out-of-phase with the first polarizer to block substantially all of the incident polarized light to form an analyzed, output light beam;
a detector adapted to receive the analyzed output light beam and produce an output signal; and
a lock-in amplifier adapted to amplify the output signal and generates an amplitude and phase of the output signal, where the lock-in frequency is the frequency of the periodically varying magnetic field or a harmonic thereof.

12. The apparatus of claim 11, further including a sample delivery system for supplying a sample to the flow cell.

13. The apparatus of claim 12, wherein the sample delivery system is an analytical separation apparatus or a sampling apparatus.

14. The apparatus of claim 11, further comprising a modulator adapted to modulate the polarization of the polarized beam prior to being received by the sample cell.

15. The apparatus of claim 14, wherein the lock-in amplifiers is locked to a combined frequency comprising frequency of the power supply and the frequency of the modulator.

16. The apparatus of claim 11, wherein the light source produces right and left handed circularly polarized light and where the apparatus further includes a handedness modulator that periodically changes the handedness of the light so that a circular dichroism of the analyte can be measured.

17. An apparatus for enhanced detection of optical properties of analytes, where the apparatus comprises:
a first light delivery system including a light source adapted to generate light having a narrow bandwidth and a plurality of optical fibers, each fiber adapted to carry a beam of incident light;
a first polarizer adapted to polarize the incident light beams to produce polarized light beams;
a sample cell including a plurality of sample chamber, each chamber containing a sample including a chiral analyte and each chamber adapted to receive a polarized light beam and produce an output light beam;
a magnetic field generator surrounding the cell and adapted to generate a periodically varying magnetic field across each chanter of the cell such that the analytes in the chambers are exposed to a periodically varying magnetic field as the polarized tight beam passes through the cell;
a power supply adapted to supply a periodically varying electric current to the magnetic field generator to generate the periodically varying magnetic field;
a second light delivery system including a plurality of optical fibers, each fiber adapted to receive one of the output light beams and a second polarizer or analyzer aligned substantially out-of-phase with the first polarizer to block substantially all of the incident polarized light in each output light beam to form analyzed, output light beams;
a detector adapted to receive the analyzed output light beams and produce output signals; and
a lock-in amplifier adapted to amplify the output signals and generate an amplitude and phase of each output signal, where the lock-in frequency is the frequency of periodically varying magnetic field or a harmonic thereof.

18. The apparatus of claim 17, further comprising a modulator adapted to modulate the polarization of the polarized beam prior to being received by the sample cell.

19. The apparatus of claim 18, wherein the lock-in amplifiers is locked to a combined frequency comprising frequency of the power supply and the frequency of the modulator.

* * * * *